United States Patent [19]

Nash et al.

[11] Patent Number: 5,702,919
[45] Date of Patent: Dec. 30, 1997

[54] DNA ENCODING CANINE GRANULOCYTE MACROPHAGE COLONY STIMULATING FACTOR

[75] Inventors: Richard A. Nash; Rainer Storb, both of Seattle, Wash.

[73] Assignee: Fred Hutchinson Cancer Research Center, Seattle, Wash.

[21] Appl. No.: 259,696

[22] Filed: Jun. 14, 1994

Related U.S. Application Data

[63] Continuation of Ser. No. 616,678, Nov. 21, 1990, abandoned.
[51] Int. Cl.[6] .................... C12N 15/27; C07K 14/535
[52] U.S. Cl. .................... 435/69.5; 536/23.5; 435/320.1; 435/172.3; 435/252.3; 435/240.1; 435/254.2
[58] Field of Search .................... 536/23.1, 23.5; 435/252.3, 320.1, 69.5, 172.3, 240.1, 254.2

[56] References Cited

PUBLICATIONS

Vowie et al. 1990. Science 247: 1306–1310.

Primary Examiner—Vasu S. Jagannathan
Assistant Examiner—Elizabeth C. Kemmerer
Attorney, Agent, or Firm—Christensen O'Connor Johnson & Kindness PLLC

[57] ABSTRACT

Canine granulocyte macrophage colony stimulating factor (caGM-CSF) corresponding to that found in canine serum and/or tissues, structural variants thereof, genes that encode these materials, related expression vectors and cells, recombinant methods for making caGM-CSF, and veterinary treatments therewith.

13 Claims, 14 Drawing Sheets

```
        -15                      -10                      -5
Met Trp Leu Gln Asn Leu Leu Phe Leu Gly Thr Val Val Cys Ser Ile 1                   5                      10                      15
Ser Ala Pro Thr Arg Ser Pro Thr Leu Val Thr Arg Pro Ser Gln His 20                      25                      30
Val Asp Ala Ile Gln Glu Ala Leu Ser Leu Leu Asn Asn Ser Asn Asp 35                      40                      45
Val Thr Ala Val Met Asn Lys Ala Val Lys Val Val Ser Glu Val Phe 50                      55                      60
Asp Pro Glu Gly Pro Thr Cys Leu Glu Thr Arg Leu Gln Leu Tyr Lys 65                      70                      75
Glu Gly Leu Gln Gly Ser Leu Thr Ser Leu Lys Asn Pro Leu Thr Met 80                      85                      90                      95
Met Ala Asn His Tyr Lys Gln His Cys Pro Pro Thr Pro Glu Ser Pro 100                     105                     110
Cys Ala Thr Gln Asn Ile Asn Phe Lys Ser Phe Lys Glu Asn Leu Lys 115                     120                     125
Asp Phe Leu Phe Asn Ile Pro Phe Asp Cys Trp Lys Pro Val Lys Lys
```

Fig. 1A

```
        1                   5                      10                      15
    Ala Pro Thr Arg Ser Pro Thr Leu Val Thr Arg Pro Ser Gln His 20              25                  30
Val Asp Ala Ile Gln Glu Ala Leu Ser Leu Leu Asn Asn Ser Asn Asp 35              40                  45
Val Thr Ala Val Met Asn Lys Ala Val Lys Val Val Ser Glu Val Phe 50              55                  60
Asp Pro Glu Gly Pro Thr Cys Leu Glu Thr Arg Leu Gln Leu Tyr Lys 65              70                  75
Glu Gly Leu Gln Gly Ser Leu Thr Ser Leu Lys Asn Pro Leu Thr Met 80              85                  90                      95
Met Ala Asn His Tyr Lys Gln His Cys Pro Pro Thr Pro Glu Ser Pro 100             105                 110
Cys Ala Thr Gln Asn Ile Asn Phe Lys Ser Phe Lys Glu Asn Leu Lys 115             120                 125
Asp Phe Leu Phe Asn Ile Pro Phe Asp Cys Trp Lys Pro Val Lys Lys
```

Fig. 1B

```
                    -15                 -10                  -5
          Met Trp Leu Gln Asn Leu Leu Phe Leu Gly Thr Val Val Cys Ser
       AG AGG ATG TGG CTG CAG AAC CTG CTT TTC TTG GGC ACT GTG GTC TGC AGC    51
            1              5                  10
 Ile Ser Ala Pro Thr Arg Ser Pro Thr Leu Val Thr Arg Pro Ser Gln
 ATC TCT GCA CCC ACC CGC TCA CCC ACC CTT GTC ACT CGG CCC TCT CAG             99
 15             20                 25                 30
 His Val Asp Ala Ile Gln Glu Ala Leu Ser Leu Leu Asn Asn Ser Asn
 CAC GTG GAT GCC ATC CAG GAA GCC CTG AGC CTT TTG AAC AAC AGT AAT            147
                35                 40                 45
 Asp Val Thr Ala Val Met Asn Lys Ala Val Lys Val Val Ser Glu Val
 GAC GTG ACT GCT GTG ATG AAT AAA GCA GTA AAA GTG GTC TCT GAA GTG            195
            50                 55                 60
 Phe Asp Pro Glu Gly Pro Thr Cys Leu Glu Thr Arg Leu Gln Leu Tyr
 TTT GAC CCT GAG GGG CCA ACA TGC CTG GAG ACC CGC CTA CAG CTG TAC            243
            65                 70                 75
 Lys Glu Gly Leu Gln Gly Ser Leu Thr Ser Leu Lys Asn Pro Leu Thr
 AAG GAG GGC CTG CAG GGC AGC CTC ACC AGC CTC AAG AAT CCC TTA ACC            291
        80                 85                 90
 Met Met Ala Asn His Tyr Lys Gln His Cys Pro Pro Thr Pro Glu Ser
 ATG ATG GCC AAT CAC TAT AAG CAG CAC TGT CCC CCT ACC CCG GAA TCT            339
 95                100                105                110
 Pro Cys Ala Thr Gln Asn Ile Asn Phe Lys Ser Phe Lys Glu Asn Leu
 CCC TGT GCA ACC CAG AAT ATT AAC TTC AAA AGT TTC AAA GAG AAC CTG            387
            115                120                125
 Lys Asp Phe Leu Phe Asn Ile Pro Phe Asp Cys Trp Lys Pro Val Lys
 AAG GAT TTT CTG TTT AAC ATC CCC TTT GAC TGC TGG AAA CCA GTC AAG            435
 Lys
 AAG  TGAGGCAGAC CAGTCCAGCC AGGAGCCAGC CCAGTCCAGC CAGAAGCCAG                488
 CCCTGAGAGC ATACCTCATA CCTCACAAGT CACTGCCTTT CTACCCATGG ATTGCTGAAA          548
 CTCAGGATCT TCACCTTTGA GGGACACCGG GTGGACCAGG GCAGTAGAGG GGGCATGGAC          608
 TTGCTCTGGC CATGCTGCCC GGATACCAGC TTGGTATGGG GAGCGGGGAA TGTTTTATAC          668
 TGGCAGGGAT CAGTAATATT TATTTATATA TTATGTATT TTAATATTTA TTTATTTATT           728
 TATTTAAGAT CATACTCTGT ATTTATTCAA GACATTTTAC TATTATAATA AATTATTAAA          788
 AGCCTGTTAA AAAAAAAAA A                                                    804
```

Fig. 2A

```
         1                   5                    10
    Ala Pro Thr Arg Ser Pro Thr Leu Val Thr Arg Pro Ser Gln
    GCA CCC ACC CGC TCA CCC ACC CTT GTC ACT CGG CCC TCT CAG
15                  20                   25                   30
His Val Asp Ala Ile Gln Glu Ala Leu Ser Leu Leu Asn Asn Ser Asn
CAC GTG GAT GCC ATC CAG GAA GCC CTG AGC CTT TTG AAC AAC AGT AAT
              35                   40                   45
Asp Val Thr Ala Val Met Asn Lys Ala Val Lys Val Val Ser Glu Val
GAC GTG ACT GCT GTG ATG AAT AAA GCA GTA AAA GTG GTC TCT GAA GTG
          50                   55                   60
Phe Asp Pro Glu Gly Pro Thr Cys Leu Glu Thr Arg Leu Gln Leu Tyr
TTT GAC CCT GAG GGG CCA ACA TGC CTG GAG ACC CGC CTA CAG CTG TAC
      65                   70                   75
Lys Glu Gly Leu Gln Gly Ser Leu Thr Ser Leu Lys Asn Pro Leu Thr
AAG GAG GGC CTG CAG GGC AGC CTC ACC AGC CTC AAG AAT CCC TTA ACC
   80                   85                   90
Met Met Ala Asn His Tyr Lys Gln His Cys Pro Pro Thr Pro Glu Ser
ATG ATG GCC AAT CAC TAT AAG CAG CAC TGT CCC CCT ACC CCG GAA TCT
95                  100                  105                  110
Pro Cys Ala Thr Gln Asn Ile Asn Phe Lys Ser Phe Lys Glu Asn Leu
CCC TGT GCA ACC CAG AAT ATT AAC TTC AAA AGT TTC AAA GAG AAC CTG
              115                  120                  125
Lys Asp Phe Leu Phe Asn Ile Pro Phe Asp Cys Trp Lys Pro Val Lys
AAG GAT TTT CTG TTT AAC ATC CCC TTT GAC TGC TGG AAA CCA GTC AAG
Lys
AAG TGAGGCAGAC CAGTCCAGCC AGGAGCCAGC CCAGTCCAGC CAGAAGCCAG
CCCTGAGAGC ATACCTCATA CCTCACAAGT CACTGCCTTT CTACCCATGG ATTGCTGAAA
CTCAGGATCT TCACCTTTGA GGGACACCGG GTGGACCAGG GCAGTAGAGG GGGCATGGAC
TTGCTCTGGC CATGCTGCCC GGATACCAGC TTGGTATGGG GAGCGGGGAA TGTTTTATAC
TGGCAGGGAT CAGTAATATT TATTTATATA TTTATGTATT TTAATATTTA TTTATTTATT
TATTTAAGAT CATACTCTGT ATTTATTCAA GACATTTTAC TATTATAATA AATTATTAAA
AGCCTGTTAA AAAAAAAAA A
```

Fig. 2B

PCR to Construct Full - Length cDNA

PRIMER #1 →

EXON 1
5'——————3'
3'——————5'

5'——————3'
3'——————5'
PARTIAL cDNA

← PRIMER #2

1ST CYCLE:

MELT
ANNEAL
5' EXTEND

AMPLIFICATION
OF FULL-LENGTH
TEMPLATES

Fig. 3.

AGGAGG

| | |
|---|---|
| ATG TGG CTG CAG AAC CTG CTT TTC TTG GGC ACT GTG GTC TGC AGC<br>M   W   L   Q   N   L   L   F   L   G   T   V   V   C   S | 51 |
| ATC TCT GCA CCC ACC CGC TCA CCC ACC CTT GTC ACT CGG CCC TCT<br>I   S   A   P   T   R   S   P   T   L   V   T   R   P   S | 96 |
| CAG CAC GTG GAT GCC ATC CAG GAA GCC CTG AGC CTT TTG AAC AAC<br>Q   H   V   D   A   I   Q   E   A   L   S   L   L   N   N | 141 |
| AGT AAT GAC GTG ACT GCT GTG ATG AAT AAA GCA GTA AAA GTG GTC<br>S   N   D   V   T   A   V   M   N   K   A   V   K   V   V | 186 |
| TCT GAA GTG TTT GAC CCT GAG GGG CCA ACA TGC CTG GAG ACC CGC<br>S   E   V   F   D   P   E   G   P   T   C   L   E   T   R | 231 |
| CTA CAG CTG TAC AAG GAG GGC CTG CAG GGC AGC CTC ACC AGC CTC<br>L   Q   L   Y   K   E   G   L   Q   G   S   L   T   S   L | 276 |
| AAG AAT CCC TTA ACC ATG ATG GCC AAT CAC TAT AAG CAG CAC TGT<br>K   N   P   L   T   M   M   A   N   H   Y   K   Q   H   C | 321 |
| CCC CCT ACC CCG GAA TCT CCC TGT GCA ACC CAG AAT ATT AAC TTC<br>P   P   T   P   E   S   P   C   A   T   Q   N   I   N   F | 366 |
| AAA AGT TTC AAA GAG AAC CTG AAG GAT TTT CTG TTT AAC ATC CCC<br>K   S   F   K   E   N   L   K   D   F   L   F   N   I   P | 411 |
| TTT GAC TGC TGG AAA CCA GTC AAG AAG TGA<br>F   D   C   W   K   P   V   K   K   * | 438 |

```
                  GGCAGACCA  GTCCAGCCAG  GAGCCAGCCC  AGTCCAGCCA
GAAGCCAGCC  CTGAGAGCAT  ACCTCATACC  TCACAAGTCA  CTGCCTTTCT  ACCCATGGAT
TGCTGAAACT  CAGGATCTTC  ACCTTTGAGG  GACACCGGGT  GGACCAGGGC  AGTAGAGGGG
GCATGGACTT  GCTCTGGCCA  TGCTGCCCGG  ATACCAGCTT  GGTATGGGGA  GCGGGGAATG
TTTTATACTG  GCAGGGATCA  GTAATATTTA  TTTATATATT  TATGTATTTT  AATATTTATT
TATTTATTTA  TTTAAGATCA  TACTCTGTAT  TTATTCAAGA  CATTTTACTA  TTATAATAAA
TTATTAAAAG  CCTGTTAAAA  AAAAAAAA
```

Fig. 4

```
          ↓                                                            *
CAGMCSF   MWLQNLLFLGTVVCSISAPTRSPTLVTRPSQHVDAIQEALSLLNNSNDVTAVMNKAVKVV 60
                                                                       *           *
HUMAN     ----S--L----A------A---SPS-Q-WE--N-----RR---L-R-TA-E--ET-E-I 60
                                                                       *           *
BOVINE    -------L-------F-----P-NTA---W------K-------H-S-TD----DT.E-- 59

MOUSE     ----------I--Y-L-------IT----WK--E--K---N--D...-MPVTL-EE-E-- 57

■                                          ■         ■
CAGMCSF   SEVFDREGPTCLETRLQLYKEGLQGSLTSLKNPLTMMANHYKQHCPPTPESPCATQNINF 120

HUMAN     --M--LQE----Q---E---Q--R----K--G------S-----------TS----I-T- 120

BOVINE    --K--SQE----Q---K---N---------MGS-----T--EK-------TS-G--F-S- 119
                                   *          *
MOUSE     -NE-SFKKL--VQ---KIFEQ--R-NF-K--GA-N-T-SY-QTY------TD-E--VTTY 117

■
CAGMCSF   KSFKENLKDFLFNIPFDCWKPVKK 144

HUMAN     E----------LV------E---E 144

BOVINE    -N---D--E---I------E-A-- 143

MOUSE     AD-IDS--T--TD---E-K----- 141
```

-- identical amino acids as caGM-CSF
.. gaps to maximize alignment
↓↓ arrows bracket signal peptide
** indicate N-glycosylation
■■ cysteine
— underlined functional system

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 144 amino acids
        ( B ) TYPE: amino acid
        ( C ) STRANDEDNESS:
        ( D ) TOPOLOGY: linear ( i i ) MOLECULE TYPE: protein
        ( A ) DESCRIPTION: see Figure 1A ( x i ) SEQUENCE DESCRIPTION: SEQ ID NO:1:

```
Met Trp Leu Gln Asn Leu Leu Phe Leu Gly Thr Val Val Cys Ser Ile
 1               5                  10                  15
Ser Ala Pro Thr Arg Ser Pro Thr Leu Val Thr Arg Pro Ser Gln His
            20                  25                  30
Val Asp Ala Ile Gln Glu Ala Leu Ser Leu Leu Asn Asn Ser Asn Asp
        35                  40                  45
Val Thr Ala Val Met Asn Lys Ala Val Lys Val Val Ser Glu Val Phe
    50                  55                  60
Asp Pro Glu Gly Pro Thr Cys Leu Glu Thr Arg Leu Gln Leu Tyr Lys
65                  70                  75                  80
Glu Gly Leu Gln Gly Ser Leu Thr Ser Leu Lys Asn Pro Leu Thr Met
                85                  90                  95
Met Ala Asn His Tyr Lys Gln His Cys Pro Pro Thr Pro Glu Ser Pro
            100                 105                 110
Cys Ala Thr Gln Asn Ile Asn Phe Lys Ser Phe Lys Glu Asn Leu Lys
        115                 120                 125
Asp Phe Leu Phe Asn Ile Pro Phe Asp Cys Trp Lys Pro Val Lys Lys
    130                 135                 140
```

( 2 ) INFORMATION FOR SEQ ID NO:2:

( i ) SEQUENCE CHARACTERISTICS:
        ( A ) LENGTH: 127 amino acids
        ( B ) TYPE: amino acid
        ( C ) STRANDEDNESS:
        ( D ) TOPOLOGY: linear ( i i ) MOLECULE TYPE: protein
        ( A ) DESCRIPTION: see Figure 1B ( x i ) SEQUENCE DESCRIPTION: SEQ ID NO:2:

```
Ala Pro Thr Arg Ser Pro Thr Leu Val Thr Arg Pro Ser Gln His Val
 1               5                  10                  15
Asp Ala Ile Gln Glu Ala Leu Ser Leu Leu Asn Asn Ser Asn Asp Val
            20                  25                  30
```

```
Thr Ala Val Met Asn Lys Ala Val Lys Val Val Ser Glu Val Phe Asp
        35              40              45

Pro Glu Gly Pro Thr Cys Leu Glu Thr Arg Leu Gln Leu Tyr Lys Glu
    50              55              60

Gly Leu Gln Gly Ser Leu Thr Ser Leu Lys Asn Pro Leu Thr Met Met
65              70              75                      80

Ala Asn His Tyr Lys Gln His Cys Pro Pro Thr Pro Glu Ser Pro Cys
            85              90                      95

Ala Thr Gln Asn Ile Asn Phe Lys Ser Phe Lys Glu Asn Leu Lys Asp
            100             105             110

Phe Leu Phe Asn Ile Pro Phe Asp Cys Trp Lys Pro Val Lys Lys
        115             120             125
```

(2) INFORMATION FOR SEQ ID NO:3:

(i) SEQUENCE CHARACTERISTICS:
        (A) LENGTH: 128 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:3:

```
Met Ala Pro Thr Arg Ser Pro Thr Leu Val Thr Arg Pro Ser Gln His
1               5               10              15

Val Asp Ala Ile Gln Glu Ala Leu Ser Leu Leu Asn Asn Ser Asn Asp
            20              25              30

Val Thr Ala Val Met Asn Lys Ala Val Lys Val Val Ser Glu Val Phe
        35              40              45

Asp Pro Glu Gly Pro Thr Cys Leu Glu Thr Arg Leu Gln Leu Tyr Lys
    50              55              60

Glu Gly Leu Gln Gly Ser Leu Thr Ser Leu Lys Asn Pro Leu Thr Met
65              70              75                      80

Met Ala Asn His Tyr Lys Gln His Cys Pro Pro Thr Pro Glu Ser Pro
            85              90                      95

Cys Ala Thr Gln Asn Ile Asn Phe Lys Ser Phe Lys Glu Asn Leu Lys
            100             105             110

Asp Phe Leu Phe Asn Ile Pro Phe Asp Cys Trp Lys Pro Val Lys Lys
        115             120             125
```

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:4:

```
Glu Ala Leu Ser Leu Leu Asn Asn Ser Asn Asp
1               5                       10
```

(2) INFORMATION FOR SEQ ID NO:5:

(i) SEQUENCE CHARACTERISTICS:
        (A) LENGTH: 17 amino acids
        (B) TYPE: amino acid
        (C) STRANDEDNESS:
        (D) TOPOLOGY: linear ( i i ) MOLECULE TYPE: peptide ( x i ) SEQUENCE DESCRIPTION: SEQ ID NO:5:

```
Thr Met Met Ala Asn His Tyr Lys Gln His Cys Pro Pro Thr Pro Glu
 1               5                  10                      15

Ser
```

( 2 ) INFORMATION FOR SEQ ID NO:6:

( i ) SEQUENCE CHARACTERISTICS:
( A ) LENGTH: 809 base pairs
( B ) TYPE: nucleic acid
( C ) STRANDEDNESS: single
( D ) TOPOLOGY: linear ( i i ) MOLECULE TYPE: cDNA
( A ) DESCRIPTION: see Figure 2A ( i x ) FEATURE:
( A ) NAME/KEY: CDS
( B ) LOCATION: 7..438

( x i ) SEQUENCE DESCRIPTION: SEQ ID NO:6:

```
AGGAGG ATG TGG CTG CAG AAC CTG CTT TTC TTG GGC ACT GTG GTC TGC         48
       Met Trp Leu Gln Asn Leu Leu Phe Leu Gly Thr Val Val Cys
        1               5                       10

AGC ATC TCT GCA CCC ACC CGC TCA CCC ACC CTT GTC ACT CGG CCC TCT        96
Ser Ile Ser Ala Pro Thr Arg Ser Pro Thr Leu Val Thr Arg Pro Ser
 15              20                  25                      30

CAG CAC GTG GAT GCC ATC CAG GAA GCC CTG AGC CTT TTG AAC AAC AGT       144
Gln His Val Asp Ala Ile Gln Glu Ala Leu Ser Leu Leu Asn Asn Ser
                 35                  40                  45

AAT GAC GTG ACT GCT GTG ATG AAT AAA GCA GTA AAA GTG GTC TCT GAA       192
Asn Asp Val Thr Ala Val Met Asn Lys Ala Val Lys Val Val Ser Glu
             50                  55                  60

GTG TTT GAC CCT GAG GGG CCA ACA TGC CTG GAG ACC CGC CTA CAG CTG       240
Val Phe Asp Pro Glu Gly Pro Thr Cys Leu Glu Thr Arg Leu Gln Leu
         65                  70                  75

TAC AAG GAG GGC CTG CAG GGC AGC CTC ACC AGC CTC AAG AAT CCC TTA       288
Tyr Lys Glu Gly Leu Gln Gly Ser Leu Thr Ser Leu Lys Asn Pro Leu
     80                  85                  90

ACC ATG ATG GCC AAT CAC TAT AAG CAG CAC TGT CCC CCT ACC CCG GAA       336
Thr Met Met Ala Asn His Tyr Lys Gln His Cys Pro Pro Thr Pro Glu
 95             100                 105                    110

TCT CCC TGT GCA ACC CAG AAT ATT AAC TTC AAA AGT TTC AAA GAG AAC       384
Ser Pro Cys Ala Thr Gln Asn Ile Asn Phe Lys Ser Phe Lys Glu Asn
                115                 120                 125

CTG AAG GAT TTT CTG TTT AAC ATC CCC TTT GAC TGC TGG AAA CCA GTC       432
Leu Lys Asp Phe Leu Phe Asn Ile Pro Phe Asp Cys Trp Lys Pro Val
            130                 135                 140

AAG AAG TGAGGCAGAC CAGTCCAGCC AGGAGCCAGC CCAGTCCAGC CAGAAGCCAG        488
Lys Lys

CCCTGAGAGC ATACCTCATA CCTCACAAGT CACTGCCTTT CTACCCATGG ATTGCTGAAA     548

CTCAGGATCT TCACCTTTGA GGGACACCGG GTGGACCAGG GCAGTAGAGG GGCATGGAC      608

TTGCTCTGGC CATGCTGCCC GGATACCAGC TTGGTATGGG GAGCGGGGAA TGTTTATAC      668

TGGCAGGGAT CAGTAATATT TATTTATATA TTTATGTATT TTAATATTTA TTTATTTATT     728

TATTTAAGAT CATACTCTGT ATTTATTCAA GACATTTTAC TATTATAATA AATTATTAAA     788

AGCCTGTTAA AAAAAAAAA A                                                809
```

( 2 ) INFORMATION FOR SEQ ID NO:7:

( i ) SEQUENCE CHARACTERISTICS:
  ( A ) LENGTH: 752 base pairs
  ( B ) TYPE: nucleic acid
  ( C ) STRANDEDNESS: single
  ( D ) TOPOLOGY: linear ( i i ) MOLECULE TYPE: cDNA
  ( A ) DESCRIPTION: see Figure 2B ( i x ) FEATURE:
  ( A ) NAME/KEY: CDS
  ( B ) LOCATION: 1..381

( x i ) SEQUENCE DESCRIPTION: SEQ ID NO:7:

| GCA | CCC | ACC | CGC | TCA | CCC | ACC | CTT | GTC | ACT | CGG | CCC | TCT | CAG | CAC | GTG | 48 |
| Ala | Pro | Thr | Arg | Ser | Pro | Thr | Leu | Val | Thr | Arg | Pro | Ser | Gln | His | Val | |
| 1 | | | | 5 | | | | | 10 | | | | | 15 | | |

| GAT | GCC | ATC | CAG | GAA | GCC | CTG | AGC | CTT | TTG | AAC | AAC | AGT | AAT | GAC | GTG | 96 |
| Asp | Ala | Ile | Gln | Glu | Ala | Leu | Ser | Leu | Leu | Asn | Asn | Ser | Asn | Asp | Val | |
| | | 20 | | | | | 25 | | | | | 30 | | | | |

| ACT | GCT | GTG | ATG | AAT | AAA | GCA | GTA | AAA | GTG | GTC | TCT | GAA | GTG | TTT | GAC | 144 |
| Thr | Ala | Val | Met | Asn | Lys | Ala | Val | Lys | Val | Val | Ser | Glu | Val | Phe | Asp | |
| | | 35 | | | | | 40 | | | | | 45 | | | | |

| CCT | GAG | GGG | CCA | ACA | TGC | CTG | GAG | ACC | CGC | CTA | CAG | CTG | TAC | AAG | GAG | 192 |
| Pro | Glu | Gly | Pro | Thr | Cys | Leu | Glu | Thr | Arg | Leu | Gln | Leu | Tyr | Lys | Glu | |
| | 50 | | | | | 55 | | | | | 60 | | | | | |

| GGC | CTG | CAG | GGC | AGC | CTC | ACC | AGC | CTC | AAG | AAT | CCC | TTA | ACC | ATG | ATG | 240 |
| Gly | Leu | Gln | Gly | Ser | Leu | Thr | Ser | Leu | Lys | Asn | Pro | Leu | Thr | Met | Met | |
| 65 | | | | | 70 | | | | | 75 | | | | | 80 | |

| GCC | AAT | CAC | TAT | AAG | CAG | CAC | TGT | CCC | CCT | ACC | CCG | GAA | TCT | CCC | TGT | 288 |
| Ala | Asn | His | Tyr | Lys | Gln | His | Cys | Pro | Pro | Thr | Pro | Glu | Ser | Pro | Cys | |
| | | | | 85 | | | | | 90 | | | | | 95 | | |

| GCA | ACC | CAG | AAT | ATT | AAC | TTC | AAA | AGT | TTC | AAA | GAG | AAC | CTG | AAG | GAT | 336 |
| Ala | Thr | Gln | Asn | Ile | Asn | Phe | Lys | Ser | Phe | Lys | Glu | Asn | Leu | Lys | Asp | |
| | | | 100 | | | | | 105 | | | | | 110 | | | |

| TTT | CTG | TTT | AAC | ATC | CCC | TTT | GAC | TGC | TGG | AAA | CCA | GTC | AAG | AAG | | 381 |
| Phe | Leu | Phe | Asn | Ile | Pro | Phe | Asp | Cys | Trp | Lys | Pro | Val | Lys | Lys | | |
| | | 115 | | | | | 120 | | | | | 125 | | | | |

| TGAGGCAGAC | CAGTCCAGCC | AGGAGCCAGC | CCAGTCCAGC | CAGAAGCCAG | CCCTGAGAGC | 441 |
| ATACCTCATA | CCTCACAAGT | CACTGCCTTT | CTACCCATGG | ATTGCTGAAA | CTCAGGATCT | 501 |
| TCACCTTTGA | GGGACACCGG | GTGGACCAGG | GCAGTAGAGG | GGGCATGGAC | TTGCTCTGGC | 561 |
| CATGCTGCCC | GGATACCAGC | TTGGTATGGG | GAGCGGGGAA | TGTTTTATAC | TGGCAGGGAT | 621 |
| CAGTAATATT | TATTTATATA | TTTATGTATT | TTAATATTTA | TTTATTTATT | TATTTAAGAT | 681 |
| CATACTCTGT | ATTTATTCAA | GACATTTTAC | TATTATAATA | AATTATTAAA | AGCCTGTTAA | 741 |
| AAAAAAAAA | A | | | | | 752 |

( 2 ) INFORMATION FOR SEQ ID NO:8:

( i ) SEQUENCE CHARACTERISTICS:
    ( A ) LENGTH: 809 base pairs
    ( B ) TYPE: nucleic acid
    ( C ) STRANDEDNESS: single
    ( D ) TOPOLOGY: linear ( i i ) MOLECULE TYPE: cDNA
    ( A ) DESCRIPTION: see Figure 4

( i x ) FEATURE:
    ( A ) NAME/KEY: CDS
    ( B ) LOCATION: 7..438

( x i ) SEQUENCE DESCRIPTION: SEQ ID NO:8:

| | | | | | | | | | | | | | | | | |
|---|---|---|---|---|---|---|---|---|---|---|---|---|---|---|---|---|
| AGGAGG | ATG | TGG | CTG | CAG | AAC | CTG | CTT | TTC | TTG | GGC | ACT | GTG | GTC | TGC | | 48 |
| | Met | Trp | Leu | Gln | Asn | Leu | Leu | Phe | Leu | Gly | Thr | Val | Val | Cys | | |
| | | | 130 | | | | | 135 | | | | | 140 | | | |
| AGC | ATC | TCT | GCA | CCC | ACC | CGC | TCA | CCC | ACC | CTT | GTC | ACT | CGG | CCC | TCT | 96 |
| Ser | Ile | Ser | Ala | Pro | Thr | Arg | Ser | Pro | Thr | Leu | Val | Thr | Arg | Pro | Ser | |
| | | 145 | | | | | 150 | | | | | 155 | | | | |
| CAG | CAC | GTG | GAT | GCC | ATC | CAG | GAA | GCC | CTG | AGC | CTT | TTG | AAC | AAC | AGT | 144 |
| Gln | His | Val | Asp | Ala | Ile | Gln | Glu | Ala | Leu | Ser | Leu | Leu | Asn | Asn | Ser | |
| | | 160 | | | | | 165 | | | | | 170 | | | | |
| AAT | GAC | GTG | ACT | GCT | GTG | ATG | AAT | AAA | GCA | GTA | AAA | GTG | GTC | TCT | GAA | 192 |
| Asn | Asp | Val | Thr | Ala | Val | Met | Asn | Lys | Ala | Val | Lys | Val | Val | Ser | Glu | |
| | | 175 | | | | | 180 | | | | | 185 | | | | |
| GTG | TTT | GAC | CCT | GAG | GGG | CCA | ACA | TGC | CTG | GAG | ACC | CGC | CTA | CAG | CTG | 240 |
| Val | Phe | Asp | Pro | Glu | Gly | Pro | Thr | Cys | Leu | Glu | Thr | Arg | Leu | Gln | Leu | |
| 190 | | | | | 195 | | | | | 200 | | | | | 205 | |
| TAC | AAG | GAG | GGC | CTG | CAG | GGC | AGC | CTC | ACC | AGC | CTC | AAG | AAT | CCC | TTA | 288 |
| Tyr | Lys | Glu | Gly | Leu | Gln | Gly | Ser | Leu | Thr | Ser | Leu | Lys | Asn | Pro | Leu | |
| | | | | 210 | | | | | 215 | | | | | 220 | | |
| ACC | ATG | ATG | GCC | AAT | CAC | TAT | AAG | CAG | CAC | TGT | CCC | CCT | ACC | CCG | GAA | 336 |
| Thr | Met | Met | Ala | Asn | His | Tyr | Lys | Gln | His | Cys | Pro | Pro | Thr | Pro | Glu | |
| | | | 225 | | | | | 230 | | | | | 235 | | | |
| TCT | CCC | TGT | GCA | ACC | CAG | AAT | ATT | AAC | TTC | AAA | AGT | TTC | AAA | GAG | AAC | 384 |
| Ser | Pro | Cys | Ala | Thr | Gln | Asn | Ile | Asn | Phe | Lys | Ser | Phe | Lys | Glu | Asn | |
| | | 240 | | | | | 245 | | | | | 250 | | | | |
| CTG | AAG | GAT | TTT | CTG | TTT | AAC | ATC | CCC | TTT | GAC | TGC | TGG | AAA | CCA | GTC | 432 |
| Leu | Lys | Asp | Phe | Leu | Phe | Asn | Ile | Pro | Phe | Asp | Cys | Trp | Lys | Pro | Val | |
| | 255 | | | | | 260 | | | | | 265 | | | | | |
| AAG | AAG | TGAGGCAGAC | | CAGTCCAGCC | | AGGAGCCAGC | | CCAGTCCAGC | | CAGAAGCCAG | | | | | | 488 |
| Lys | Lys | | | | | | | | | | | | | | | |
| 270 | | | | | | | | | | | | | | | | |

| | |
|---|---|
| CCCTGAGAGC ATACCTCATA CCTCACAAGT CACTGCCTTT CTACCCATGG ATTGCTGAAA | 548 |
| CTCAGGATCT TCACCTTTGA GGGACACCGG GTGGACCAGG GCAGTAGAGG GGGCATGGAC | 608 |
| TTGCTCTGGC CATGCTGCCC GGATACCAGC TTGGTATGGG GAGCGGGGAA TGTTTTATAC | 668 |
| TGGCAGGGAT CAGTAATATT TATTTATATA TTTATGTATT TTAATATTTA TTTATTTATT | 728 |
| TATTTAAGAT CATACTCTGT ATTTATTCAA GACATTTTAC TATTATAATA AATTATTAAA | 788 |
| AGCCTGTTAA AAAAAAAAA A | 809 |

( 2 ) INFORMATION FOR SEQ ID NO:9:

( i ) SEQUENCE CHARACTERISTICS:
( A ) LENGTH: 144 amino acids
( B ) TYPE: amino acid
( C ) STRANDEDNESS:
( D ) TOPOLOGY: linear ( i i ) MOLECULE TYPE: protein
( A ) DESCRIPTION: Human GMCSF, Figure 5

( x i ) SEQUENCE DESCRIPTION: SEQ ID NO:9:

| | | | | | | | | | | | | | | |
|---|---|---|---|---|---|---|---|---|---|---|---|---|---|---|
| Met | Trp | Leu | Gln | Ser | Leu | Leu | Leu | Leu | Gly | Thr | Val | Ala | Cys | Ser | Ile |
| 1 | | | | 5 | | | | | 10 | | | | | 15 | |
| Ser | Ala | Pro | Ala | Arg | Ser | Pro | Ser | Pro | Ser | Thr | Gln | Pro | Trp | Glu | His |
| | | | 20 | | | | | 25 | | | | | 30 | | |
| Val | Asn | Ala | Ile | Gln | Glu | Ala | Arg | Arg | Leu | Leu | Asn | Leu | Ser | Arg | Asp |
| | | 35 | | | | | 40 | | | | | 45 | | | |
| Gln | Ala | Ala | Glu | Met | Asn | Glu | Thr | Val | Glu | Val | Ile | Ser | Glu | Met | Phe |
| | 50 | | | | | 55 | | | | | 60 | | | | |
| Asp | Leu | Gln | Glu | Pro | Thr | Cys | Leu | Gln | Thr | Arg | Leu | Glu | Leu | Tyr | Lys |
| 65 | | | | | 70 | | | | | 75 | | | | | 80 |

```
Gln  Gly  Leu  Arg  Gly  Ser  Leu  Thr  Lys  Leu  Lys  Gly  Pro  Leu  Thr  Met
               85                      90                      95

Met  Ala  Ser  His  Tyr  Lys  Gln  His  Cys  Pro  Pro  Thr  Pro  Glu  Thr  Ser
              100                     105                     110

Cys  Ala  Thr  Gln  Ile  Ile  Thr  Phe  Glu  Ser  Phe  Lys  Glu  Asn  Leu  Lys
              115                     120                     125

Asp  Phe  Leu  Leu  Val  Ile  Pro  Phe  Asp  Cys  Trp  Glu  Pro  Val  Lys  Glu
         130                     135                     140
```

( 2 ) INFORMATION FOR SEQ ID NO:10:

( i ) SEQUENCE CHARACTERISTICS:
        ( A ) LENGTH: 143 amino acids
        ( B ) TYPE: amino acid
        ( C ) STRANDEDNESS:
        ( D ) TOPOLOGY: linear ( i i ) MOLECULE TYPE: protein
        ( A ) DESCRIPTION: Bovine GMCSF, Figure 5

( x i ) SEQUENCE DESCRIPTION: SEQ ID NO:10:

```
Met  Trp  Leu  Gln  Asn  Leu  Leu  Leu  Gly  Thr  Val  Val  Cys  Ser  Phe
 1              5                      10                     15

Ser  Ala  Pro  Thr  Arg  Pro  Pro  Asn  Thr  Ala  Thr  Arg  Pro  Trp  Gln  His
               20                      25                      30

Val  Asp  Ala  Ile  Lys  Glu  Ala  Leu  Ser  Leu  Leu  Asn  His  Ser  Ser  Asp
              35                      40                      45

Thr  Asp  Ala  Val  Met  Asn  Asp  Thr  Glu  Val  Val  Ser  Glu  Lys  Phe  Asp
         50                      55                      60

Ser  Gln  Glu  Pro  Thr  Cys  Leu  Gln  Thr  Arg  Leu  Lys  Leu  Tyr  Lys  Asn
65                      70                      75                     80

Gly  Leu  Gln  Gly  Ser  Leu  Thr  Ser  Leu  Met  Gly  Ser  Leu  Thr  Met  Met
               85                      90                      95

Ala  Thr  His  Tyr  Glu  Lys  His  Cys  Pro  Thr  Pro  Glu  Thr  Ser  Cys
              100                     105                     110

Gly  Thr  Gln  Phe  Ile  Ser  Phe  Lys  Asn  Phe  Lys  Glu  Asp  Leu  Lys  Glu
              115                     120                     125

Phe  Leu  Phe  Ile  Ile  Pro  Phe  Asp  Cys  Trp  Glu  Pro  Ala  Lys  Lys
         130                     135                     140
```

( 2 ) INFORMATION FOR SEQ ID NO:11:

( i ) SEQUENCE CHARACTERISTICS:
        ( A ) LENGTH: 141 amino acids
        ( B ) TYPE: amino acid
        ( C ) STRANDEDNESS:
        ( D ) TOPOLOGY: linear ( i i ) MOLECULE TYPE: protein
        ( A ) DESCRIPTION: Mouse GMCSF, Figure 5

( x i ) SEQUENCE DESCRIPTION: SEQ ID NO:11:

```
Met  Trp  Leu  Gln  Asn  Leu  Leu  Phe  Leu  Gly  Ile  Val  Val  Tyr  Ser  Leu
 1              5                      10                     15

Ser  Ala  Pro  Thr  Arg  Ser  Pro  Ile  Thr  Val  Thr  Arg  Pro  Trp  Lys  His
               20                      25                      30

Val  Glu  Ala  Ile  Lys  Glu  Ala  Leu  Asn  Leu  Leu  Asp  Asp  Met  Pro  Val
              35                      40                      45

Thr  Leu  Asn  Glu  Glu  Val  Glu  Val  Val  Ser  Asn  Glu  Phe  Ser  Phe  Lys
         50                      55                      60
```

-continued

| Lys 65 | Leu | Thr | Cys | Val | Gln 70 | Thr | Arg | Leu | Lys 75 | Ile | Phe | Glu | Gln | Gly | Leu 80 |
| Arg | Gly | Asn | Phe | Thr 85 | Lys | Leu | Lys | Gly | Ala 90 | Leu | Asn | Met | Thr | Ala 95 | Ser |
| Tyr | Tyr | Gln | Thr 100 | Tyr | Cys | Pro | Pro | Thr 105 | Pro | Glu | Thr | Asp | Cys 110 | Glu | Thr |
| Gln | Val | Thr 115 | Thr | Tyr | Ala | Asp | Phe 120 | Ile | Asp | Ser | Leu | Lys 125 | Thr | Phe | Leu |
| Thr | Asp 130 | Ile | Pro | Phe | Glu | Cys 135 | Lys | Lys | Pro | Val | Lys 140 | Lys | | | |

DNA ENCODING CANINE GRANULOCYTE MACROPHAGE COLONY STIMULATING FACTOR

This is a continuation of the prior application Ser. No. 07/616,678, filed Nov. 21, 1990, abandoned, the benefit of the filing date of which is hereby claimed under 35 U.S.C. §120.

This invention was made with government support under grants CA 15704 and DK 42716 awarded by the National Institutes of Health. The government has certain rights in the invention.

FIELD OF THE INVENTION

The present invention relates to canine granulocyte macrophage colony stimulating factor (canine or caGM-CSF herein) corresponding to that found in canine serum and/or tissues. In other aspects, the invention covers, inter alia, structural variants of caGM-CSF, polynucleotides that encode caGM-CSF and its structural variants, expression vectors containing the polynucleotides, and cells transformed by the expression vectors.

BACKGROUND OF THE INVENTION

Granulocyte-macrophage colony stimulating factor (GM-CSF) is a glycoprotein that regulates proliferation and differentiation of hematopoietic progenitors [1,2]. GM-CSF is produced by lymphocytes, monocytes, endothelial cells, and fibroblasts, as well as other cell lines [3-9]. It has broad stimulating activity in vitro on hematopoietic cells, alone or in combination with other hematopoietic growth factors [10-17]. It also alters the function of relatively differentiated cells, like neutrophils and macrophages, by enhancing chemotaxis and increasing oxidative metabolism, phagocytic activity, and microbicidal activity [18-24]. In vivo studies became possible with the isolation of the cDNA for human GM-CSF and the production of the recombinant human protein [25-32]. Animal studies and clinical trials have been completed and suggest potential therapeutic uses for recombinant human GM-CSF. However, biological and preclinical questions persist about the role of this factor in the control of hemopoiesis and the optimal use either alone or in combination with other materials to reverse perturbations of hemopoiesis secondary to a disease process or to toxicity of radiation and chemotherapy. The cloning of the cDNA for GM-CSF from three species: mouse, cow, and man, has been reported [1, 37, and 2, respectively]. The biological activity of GM-CSF has been demonstrated to be highly species-restricted despite a significant nucleotide and amino acid sequence homology [13,37].

Until the work by the present inventors, no work had been reported on isolating a factor having GM-CSF activity from dogs. Several potential difficulties had to be surmounted before the present inventors succeeded in achieving the present invention. First, although GM-CSF proteins had been isolated from three other species, as mentioned above, it was unclear to what extent there would be homology between these known GM-CSF materials and that from dogs. Accordingly, it was unclear whether probes based on GM-CSF proteins associated with other species would be useful in isolating an analogous material from dogs. Second, it was unclear whether canine cells could be adequately stimulated to produce enhanced amounts of messenger RNA (mRNA) for a canine GM-CSF. Although it was previously reported that canine cells could be generally stimulated to produce a conditioned medium with stimulating activity on hematopoietic progenitors, it was not clear whether the resulting activity was due to canine GM-CSF protein in the medium, nor was there any indication at what level mRNA was being transcribed.

In spite of the above uncertainties, and other difficulties, the present inventors succeeded in isolating a full cDNA sequence corresponding to a protein having GM-CSF activity in dogs. This discovery established the basis of the present invention.

SUMMARY OF THE INVENTION

The present invention has several aspects. In a first aspect, the present invention relates to proteinaceous molecules having at least about 90% homology to an amino acid sequence corresponding to natural caGM-CSF and which have an activity of caGM-CSF. More specifically, this aspect of the present invention relates to isolated proteinaceous molecules comprising amino acid sequence I (SEQ ID NO:1), amino acid sequence II (SEQ ID NO:2), amino acid sequence III (SEQ ID NO:3), proteinaceous molecules comprising both amino acid sequence IV (SEQ ID NO:4) and amino acid sequence V (SEQ ID NO:5), and proteinaceous molecules having at least about 90% homology to these amino acid sequences.

In another aspect of the present invention, it relates to isolated polynucleotide molecules encoding the proteinaceous molecules described above.

Other aspects of the present invention relate to recombinant expression vectors capable of transferring the recited polynucleotide molecules to suitable host cells, and to cells transformed by these expression vectors.

In another aspect, the present invention relates to methods of producing the recited proteinaceous molecules by recombinant means.

In a further aspect of the present invention, it relates to pharmaceutical compositions comprising the recited proteinaceous molecules.

In yet another aspect, the present invention relates to specific binding partners to the recited proteinaceous molecules.

The above aspects of the present invention enable production of large quantities of proteinaceous molecules having canine granulocyte macrophage colony stimulating factor activity. It is contemplated that such molecules can be used, e.g., for veterinary purposes to treat dogs, as described in greater detail hereinbelow.

BRIEF DESCRIPTION OF THE DRAWINGS

FIG. 1A shows Amino Acid Sequence I (SEQ ID NO:1) corresponding to natural caGM-CSF (which includes an N-terminal 17-amino acid signal peptide);

FIG. 1B shows Amino Acid Sequence II (SEQ ID NO:2) corresponding to mature caGM-CSF without the signal peptide;

FIG. 2A shows Nucleotide Sequence I (SEQ ID NO:6), which encodes Amino Acid Sequence I (SEQ ID NO:1);

FIG. 2B shows Nucleotide Sequence No. 2 (SEQ ID NO:7), which encodes Amino Acid Sequence II (SEQ ID NO:2);

FIG. 3 shows a polymerase chain reaction used by the inventors to construct full-length cDNA corresponding to natural caGM-CSF.

FIG. 4 is the nucleotide sequence (SEQ ID NO:6) of full-length caGM-CSF cDNA. The start codon 'ATG' and stop codon 'TGA' (asterisks) flank an open reading frame of 432 base pairs with nucleotide sequence homology of 80% to the polynucleotide sequence corresponding to human GM-CSF. The nucleotide homology of the complete cDNA sequence is 65% [The amino acid homology between canine and human GM-CSF is 70%.]. The highlighted 5' region which includes the start codon is the 17-base pair sequence common to cDNA's of GM-CSF from all four different species (human, dog, mouse, cow). In the 3' untranslated region there is an AT rich sequence with an ATTTA motif that destabilizes the mRNA transcript.

FIG. 5 shows amino acid sequences of GM-CSF from four different species aligned to allow comparison and homology determination. There is an N-terminal sequence of 17 amino acids characteristic of signal sequences (arrows). Human GM-CSF (SEQ ID NO:9) is known to have two N-glycosylation sites, but canine GM-CSF has (SEQ ID NO:1) only one predicted site (asterisks). The positions of the cysteine residues are identical between canine and human GM-CSF (squares). Also show are the sequences for bovine GM-CSF (SEQ ID NO:10) and mouse GM-CSF (SEQ ID NO:11). There are regions of functional importance on human GM-CSF: amino acids 38–48 and amino acids 95–111 [47] (underlined), of which the latter has the most similarity to canine GM-CSF. Gaps (represented by dots) were introduced in sequences to maximize alignment.

To produce FIG. 8, four dogs received five courses of caGM-CSF subcutaneously twice daily for fourteen days. Doses ranged from 1 μg→50 mg/kg/day. The dog that received 1 μg/kg/day (●—●) received a second fourteen day course of treatment of 10 μg/kg/day (o—o) after a fourteen day period of rest. Peripheral blood counts for neutrophils (shown in FIG. 8A), lymphocytes (shown in FIG. 8B), monocytes (shown in FIG. 8C), and eosinophils (shown in FIG. 8D) were obtained before, during and after treatment. Increases were noted in all categories, depending on the dose of caGM-CSF received.

Figure 9:
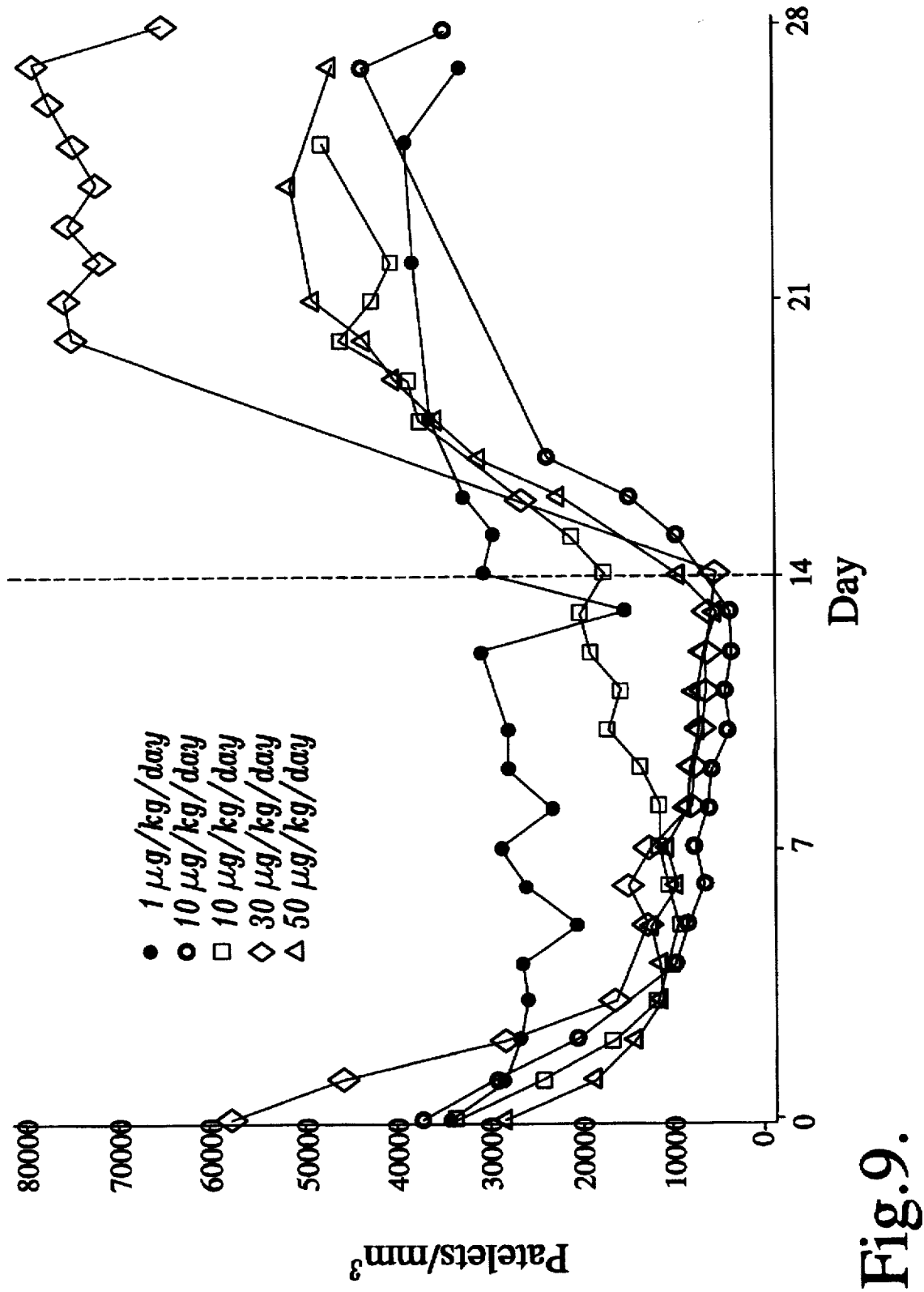

FIG. 9 shows platelet counts for 4 dogs that received 5 courses of caGM-CSF subcutaneously twice daily for 14 days. The dog that received 1 μg/kg/day (●—●) received a second 14 day course of treatment of 10 μg/kg/day (o—o) after a 14 day period of rest. Decreased platelets were noted within 24 hours of initiating treatment.

DETAILED DESCRIPTION OF THE PREFERRED EMBODIMENT

The present inventors have isolated and cloned the cDNA for canine GM-CSF. Using this cDNA, a polypeptide corresponding to canine GM-CSF has been expressed by transformed cells, and may now be used therapeutically and for in vitro and in vivo studies. The isolated cDNA is an 850 base pair sequence (SEQ ID NO:6) which encodes the naturally occurring protein having 144 amino acids, which includes the signal peptide of 17 amino acids.

The subsequent discussion herein will be facilitated by the following pertinent definitions:

"Proteinaceous molecule"—Generally, any molecule made up of a plurality of amino acids. The term is broad enough to include peptides, oligopeptides, and proteins. Typically, the amino acids in the proteinaceous material will be selected from the 20 naturally occurring amino acids. However, amino acid analogs and derivatives could also be included in the proteinaceous molecule. The proteinaceous molecule will usually be made up of about the same number of amino acids contained in naturally occurring canine GM-CSF (i.e., about 144 amino acids). In addition, however, the proteinaceous molecule may have a greater or lesser number of amino acids (for example, 144±30 amino acids), as long as the molecules retain an activity of caGM-CSF. This activity need not be quantitatively the same as the activity of the natural protein, and may be more or less than that activity, as long as it is measurable by an assay of caGM-CSF activity (see below). Preferably, such molecules will possess at least about 50% of the activity of the naturally occurring caGM-CSF without the signal peptide (Amino Acid Sequence II; SEQ ID NO:2). In some hosts, expression of recombinant caGM-CSF will result in a protein having an N-terminal methionine residue. Amino acid sequences containing such a residue on the N-terminus thereof are also within the scope of the present invention.

By "activity of caGM-CSF" is meant any activity that is measurable by an in vivo or in vitro GM-CSF assay. Qualitatively, the activity will generally be one that is possessed by the naturally occurring canine GM-CSF protein. A preferred in vivo assay for measuring granulocyte macrophage colony stimulating factor activity is referred to as a granulocyte macrophage colony forming unit (CFU-GM) assay. This assay involves measuring the number of colonies of granulocytes and macrophages from dogs formed in vitro in response to contact with a test substance. A typical assay procedure is described in Schuening et al. [38]. Other known assays may also be used. For example, in vivo assays of caGM-CSF activity can involve measuring marrow cellularity, and/or peripheral counts, in response to administration of a test substance to a dog.

By "isolated" is meant that a substance is substantially free from normally occurring impurities or other molecules, especially other proteinaceous molecules, salts, other cellular constituents, etc. Isolation may typically be carried out by standard methods in the art of nucleotide, peptide and/or protein purification or synthesis.

"Polynucleotide sequences" encompass both DNA- and RNA-containing molecules. The DNA molecules will preferably be intronless sequences (i.e., cDNA), but can contain enhancer sequences, termination sequences, and the like, to facilitate or increase expression in a particular host. Messenger RNA (mRNA) molecules are also encompassed by the term.

By "recombinant expression vector" is meant a vector (e.g., a plasmid or λ phage) that is capable of transferring polynucleotide sequences contained therein into cells of a host organism for expression of the transferred sequences. The sequences are operably linked to other sequences capable of effecting or modulating their expression. Such expression vectors must be replicable in a host organism. For example, any DNA sequence that is capable of effecting expression of a specified DNA sequence disposed therein is included in this term as it is applied to the specified sequence.

The "cells" that may be transformed by way of the vectors described above are those that are capable of expressing the polynucleotide sequences that have been transferred by the vector. Culturing conditions for such cells may be those standard in the art of recombinant protein production.

"Specific binding partners" are molecules that are capable, on a molecular level, of recognizing and interacting with the proteinaceous or polynucleotide molecules described herein; included within this term are immunological binding partners such as antibody molecules, antigen-binding fragments of antibodies (e.g., Fab and F(ab')$_2$ fragments), single chain antigen-binding molecules, and the like, whether produced by hybridoma or rDNA technology. Other proteinaceous or non-proteinaceous binding partners are also included within the broad term.

Proteinaceous Molecules

The proteinaceous molecules of this invention will now be described in greater detail. Amino Acid Sequence I (SEQ ID NO:1) corresponds to the naturally occurring canine peptide having 144 amino acids. The first 17 amino acids, extending from Met-1 to Ser-17 are believed to be a signal peptide, which is presumably cleaved by a signal peptidase in vivo or during recombinant expression using many host cells. Amino Acid Sequence II (SEQ ID NO:2) has a sequence corresponding to Amino Acid Sequence I without the signal peptide sequence. Thus, it corresponds to mature caGM-CSF.

Amino Acid Sequences III (SEQ ID NO:4) and IV (SEQ ID NO:5) correspond to amino acids 38–48 and 95–111, respectively, in Amino Acid Sequence I. These amino acid sequences are believed to be important functional regions of caGM-CSF. Amino acid sequences containing both of these sequences, preferably separated by approximately 46 amino acids (as in the natural sequences) are also part of the present invention.

The family of caGM-CSF factors provided herein also includes proteinaceous molecules in which one or more of the amino acids in the above-recited amino acid sequences has been deleted, modified, or changed to another amino acid. Site directed mutagenesis is a preferred technique enabling conversion of one amino acid to another. For example, one or more of the cysteine residues may be changed to another amino acid such as serine. One possible reason for such a change would be to eliminate one or more unwanted disulfide bonds. See, for example, U.S. Pat. No. 4,518,584.

Other contemplated specific changes in the natural amino acid sequences involve modification of the asparagine glycosylation site. Modification of the asparagine or one or both of the subsequent two amino acids (asparagine and serine in Amino Acid Sequences I and II) can eliminate glycosylation at the modified site. Thus, for example, the asparagine could be changed to a glutamine, thereby eliminating glycosylation at the site. See, for example, A. Miyajima et al., EMBO J., 5(6):1993 (1986).

The modifications of the amino acid sequences described above that form a part of the present invention are those that result in proteinaceous molecules having an activity of canine GM-CSF. Such activity may be determined using the assays described above, or equivalent standard assays. The family of proteinaceous molecules of the present invention will also generally have at least about 90% homology to amino acid sequences I, II, or III which means that several of the amino acids in each sequence may be deleted, modified, or changed (assuming the resulting proteinaceous material retains at least some activity in common with canine GM-CSF).

The proteinaceous molecules of the present invention may further be labeled by attachment to a detectable marker substance (e.g., radiolabeled with $^{125}$I) to provide reagents useful in vitro or in vivo.

Polynucleotide Sequences

The present invention is also directed to polynucleotide sequences. Preferred polynucleotide sequences are DNA molecules that encode the proteinaceous molecules of the present invention, described above. A preferred DNA sequence (SEQ ID NO:6) is the one shown in FIG. 2A herein. The novel cDNA sequence illustrated in FIG. 2A included in a plasmid has been deposited before the filing date in the American Type Culture Collection, 12301 Parklawn Drive, Rockville, Md. and given accession No. ATCC No. 40921. The cDNA of FIG. 2A is described in greater detail in the Examples section below.

It is to be recognized that more than one DNA sequence can encode the same amino acid sequence, due to the degeneracy of the genetic code; all such sequences are encompassed by the polynucleotide sequences described herein.

The method of obtaining the cDNA of FIG. 2A is described in the Examples Section below.

Polynucleotide products of the present invention may be labeled with detectable markers (such as radiolabels and non-isotopic labels such as biotin) and employed, for example, in DNA hybridization processes to locate the canine gene position and/or the position of any related gene family in a chromosomal map. They may also be used for identifying canine gene disorders at the DNA level and used as gene markers for identifying neighboring genes and their disorders.

Expression Vectors, Hosts, and Recombinant Methods

In general terms, the production of a recombinant canine GM-CSF typically involves the following:

Initially, a DNA encoding the mature protein, the preprotein (containing the signal peptide), or a fusion of the caGM-CSF protein to an additional sequence which does not destroy its activity or to an additional sequence cleavable under controlled conditions (such as treatment with a peptidase) to give an active protein, is obtained. If the sequence is uninterrupted by introns, it is suitable for expression in any host. If there are introns, expression is possible in mammalian or other eukaryotic systems capable of processing them.

Next, the isolated coding sequence is placed in operable linkage with suitable control sequences in a replicable expression vector. The vector is then used to transform a suitable host and the transformed host cultured under favorable conditions to effect the production of recombinant canine GM-CSF. Optionally, the caGM-CSF is isolated from the medium or from the cells; recovery and purification of the protein may not be necessary in instances where some impurities can be tolerated. For example, for in vitro cultivation of cells from which a lymphokine factor will be isolated for administration to a subject, complete purity is not required. However, direct use in therapy by administration to a subject would, of course, require purification of the canine GM-CSF produced.

The constructions for expression vectors operable in a variety of hosts are made using appropriate control sequences, etc., as set forth below. Generally, prokaryotic, yeast, or mammalian cells are useful as hosts. Eukaryotic cells, particularly mammalian cells, are preferred when a processing step (e.g., intron excision, glycosylation, etc.) is desired.

A variety of prokaryotic cells known to those of ordinary skill in this art may be utilized. A few exemplary strains include: *E. coli.*, *Bacillus subtilis*, and various strains of Pseudomonas.

In addition to bacteria, eukaryotic microbes, such as yeast, may also be used as host. Laboratory strains of *Saccharomyces cerevisiae*, bakers yeast, are most commonly used.

It is also possible to express genes encoding polypeptides in eukaryotic host cell cultures derived from multi-cellular organisms. Useful host cell lines include Vero, HeLa, COS, and Chinese hamster ovary (CHO) cells. Expression vectors for such cells ordinarily include promoters and control sequences compatible with mammalian cells such as, for example, the commonly used early and later promoters from Simian Virus 40 (SV40) or other viral promoters such as those derived from polyoma, adenovirus 2, bovine papilloma virus, avian sarcoma viruses, immunoglobulin promoters and heat shock promoters. Enhancer regions may also be included as desired.

Other examples of hosts, vectors, enhancers, promoters, etc., may be found in the following exemplary U.S. Pat. Nos. 4,810,643; 4,766,075; and 4,847,201, each of which is incorporated by reference herein.

Pharmaceutical Compositions

Also contemplated by the inventors as part of this invention are pharmaceutical compositions comprising effective amounts of proteinaceous molecules as described herein. The proteinaceous molecules will typically be combined with suitable diluents, agents and/or carriers useful in GM-CSF therapy. The proteinaceous molecules of the present invention may be incorporated as the sole active ingredient in such pharmaceutical compositions, or they may be combined with other active agents, such as other hematopoietic factors or drugs useful in treatment of hematopoietic disorders, such as aplastic anemia. Other lymphokines (e.g., IL-3, M-CSF, IL-1, IL-6, G-CSF, Steel locus factor) may also be incorporated in these compositions. The combination of such active ingredients (proteinaceous molecules of this invention and other active materials) may result in synergistic activity for a particular purpose, so that reduced quantities of active ingredient may be made possible.

Uses of the Proteinaceous Materials and Pharmaceutical Compositions

Granulocyte-macrophage colony stimulating factor has been demonstrated to have significant effects on both the hematopoietic and immunologic systems in humans and mice. Applications for canine GM-CSF as therapy in dogs are several. It could be used as an adjunct to existing chemotherapy or more intensive chemotherapy regimens for various oncologic disorders, especially lymphoma, to lessen the hematopoietic toxicity. It also could be used as an agent to prime host defenses against parasitic, bacterial or viral infections, with or without the additional of antibiotics. Antibiotics are a selective force in generating antibiotic-resistant microbes. Use of canine GM-CSF especially as prophylaxis, for instance, after surgery, may be effective in reducing the infection rates as well as the use of antibiotics. Certain hematopoietic conditions in the dog that are disease-related and also associated with neutropenia may also be amenable to therapy with canine GM-CSF.

The advantages of the canine species factor as therapeutic agent rather than the human-derived factor are several. The most cogent is the increased potency. GM-CSF is also an agent with multiple roles and one cannot be sure of the full-spectrum of activity with a factor derived from another species. The species-specific factor is less likely to generate an immune response with the formation of neutralizing antibodies which could limit therapeutic administration.

A representative dosage is 30–50 μg/kg/day diluted in 0.9% NaCl and administered subcutaneously. Dosages and indications for treatment would be refined as studies progressed.

Specific Binding Partners

Specific binding partners directed to the proteinaceous molecules and polypeptides of the present invention may be generated by any standard technique known to those of ordinary skill. Preferred specific binding partners are immunological binding partners such as intact antibodies and fragments thereof. The immunological binding partners are preferably monoclonal antibodies directed to a specific antigen, which are prepared by standard techniques of monoclonal antibody production.

These specific binding partners may be utilized, for example, to purify the proteinaceous materials or polynucleotides of the present invention. Specific binding partners in labeled form may be utilized to indicate the presence of the proteinaceous molecules or polynucleotides of the present invention. In one preferred embodiment, a specific binding partner of a polynucleotide of the present invention may be utilized in labeled form to locate the natural gene on a chromosome.

The invention now being generally described, the same will be better understood by reference to certain specific examples which are included herein for illustrative purposes only and are not intended to be limiting of the present invention, except where so stated.

EXAMPLES

Isolation of the Full-Length caGM-CSF cDNA

To obtain a T cell lymphocyte enriched population, peripheral blood and splenic mononuclear cells were isolated from a Ficoll-Hypaque gradient. They were then cultured for 48 hours in RPMI-1640 medium (M. A. Bioproducts) supplemented with 5% fetal calf serum (Gibco) in the presence of 1% phytohemagglutinin (Difco) and 5% pokeweed nitrogen (Gibco). Blast morphology was determined microscopically in all cultures to confirm stimulation of T-lymphocytes prior to RNA extraction on a cesium chloride gradient [39]. A cDNA library in a Lambda Zap cloning vector (Stratagene) [40] was constructed and packaged. The library was screened with the cDNA for the coding region of hGM-CSF (Genetics Institute). Probes were radiolabeled utilizing random hexamers and [$^{32}$P] αdeoxy-cytidine triphosphate [41]. Hybridization was performed in a buffer containing 35% (V/V) formamide at 37° C. over night. Nylon filters (Amersham) were washed at room temperature in 2×SSPE, 0.5% SDS and then 0.5×SSPE for 20 minutes each. Plasmids (pBluescript SK(−)) containing the canine GM-CSF cDNA were subcloned from the Lambda Zap phage by an in vivo excision process in the presence of helper virus [40].

A library of canine genomic DNA, partially digested with MboI and ligated into EMBL4 was obtained (Clontech). It was screened with a radiolabeled cDNA [41] for canine GM-CSF. Hybridization of the filters was done with 50% (V/V) formamide at 42° C. and the washes were performed at 42° C. The genomic DNA inserts were excised by Sal I and then restriction mapped. A restriction fragment that hybridized with the caGM-CSF cDNA was subcloned into pBluescript SK(−).

A full-length cDNA for caGM-CSF was made by first producing a template for Exon I from the gene through amplification by the polymerase chain reaction (PCR) [42]. Then, a second PCR was done with 2 DNA templates—the Exon I amplimer and the partial cDNA for caGM-CSF. These two templates had overlapping complementary sequences 80 bp long. The primer-linkers (20 bp/Bam HI) were oligonucleotides with complementation to a region at the start codon of Exon I and a region at the stop codon of the partial cDNA. This created the full-length 432bp coding region for the cDNA of caGM-CSF flanked by sequences for Bam HI restriction sites. See FIG. 4.

Clones were sequenced in pBluescript SK(−) using the dideoxynucleotide method [43] as described in the Sequenase (United States Biochemical) protocol for double-stranded DNA. All pBluescript SK(−) clones with the cDNA or genomic fragment inserts were initially sequenced from the flanking T3 and T7 primers. Sequence analysis was done with Genepro Version 4.2 software (Riverside Scientific Enterprises).

Genomic DNA Analysis

Genomic DNA was isolated from canine peripheral blood mononuclear cells as has been described [39]. Restriction digests were performed and DNA was electrophoresed in a 1.0% agarose gel. Southern transfer was done onto a nylon filter and hybridized with a $^{32}$P-labeled canine GM-CSF probe.

Protein Expression for In Vitro Analysis

The full-length caGM-CSF cDNA with flanking Bam HI sites was subcloned into a mammalian expression vector, pCMV. Correct orientation of the insert was determined by Pst I restriction digest for which there was one unique site in the cDNA. The pCMV/CAGM vector was sequenced with sequence-specific primers for caGM-CSF. The vector was then transfected into COS cells by the calcium phosphate precipitation method [44]. Cells were grown as described [45], and supernatant harvested at 72 hours and 120 hours.

Canine CFU-GM assays were performed as described [38] with dilutions of supernatant from COS cells transfected with pCMV/CAGM. Supernatant harvested from COS cells that had not been transfected served as one of the negative controls. Positive controls were CFU-GM assays done in the presence of post-endotoxin dog serum or human AB plasma which had been screened for activity in canine CFU-GM colony assays. Marrow mononuclear cells collected from a Ficoll-Hypaque gradient were depleted of monocytes and T-lymphocytes and cultured at $7.5 \times 10^4$ cells/ plate for 10 days at 37° C. in a humidified 10% $CO_2$ incubator in 35 mm plastic petri dishes containing 2 ml of agar medium. Agar medium consisted of an equal volume mixture of 0.6% (wt/vol) Bacto-Agar (Difco) and double-strength Dulbecco's modified Eagle's medium (Gibco) containing 40% (V/V) heat-inactivated FCS.

In Vivo Analysis

Four dogs were treated with caGM-CSF expressed in *E. coli* (protein expressed and provided by Amgen, Thousand Oaks, Calif.). Doses were administered subcutaneously twice daily. The first dog (C918) was given 1 µg/kg/day caGM-CSF for 14 days, then a 14-day rest with no treatment and then another course of 10 µg/kg/day caGM-CSF for 14 days. The other three dogs were treated with 10, 30 and 50 µg/kg/day caGM-CSF for 14 days. Baseline peripheral blood counts were established by two measurements prior to administration and then counts were followed daily. Marrow aspirations and biopsies were obtained as previously described [38] before and after 14 days of treatment. Platelet survival studies with $^{51}$Cr-labeled autologous platelets were done on dogs which received the 10 and 50 µg/kg/day doses [46].

All dogs were dewormed and vaccinated for rabies, distemper, leptospirosis, hepatitis and parvovirus. They were housed in an American Association for Accreditation of Laboratory Animal Care approved facility in standard indoor runs and provided commercial dog chow and chlorinated tap water ad libitum. Animal holding areas were maintained at 70°±2° F. with 50% ±10 relative humidity using at least 15 air changes/hour of 100% conditioned fresh air. The dogs were on a 12-hour light/dark full spectrum lighting cycle with no twilight. The protocol for this study was approved by the internal animal use committee of the Fred Hutchinson Cancer Research Center.

Results

Isolation of Full Length caGM-CSF cDNA Clone

The cDNA library that was constructed from canine peripheral blood and splenic mononuclear cells had a titre of $3 \times 10^{10}$ plaque forming units. Only 3 unique clones were isolated, all of which were incomplete cDNAs of caGM-CSF. After all clones were characterized by sequencing, it was evident that they were all incomplete at the 5' end. To obtain the remaining sequence, the incomplete cDNA for caGM-CSF was $^{32}$P-labeled and used to screen a canine genomic library.

A genomic clone was isolated that had a 12 kb insert. A 4.5 kb Bam HI-Sal I restriction fragment from the clone was identified as having the caGM-CSF gene. This fragment was subcloned into pBluescript Sk(−) for sequencing. A primer derived from the sequence of the 5' end of the longest incomplete cDNA previously isolated allowed sequencing of Exon I, completing the sequence for the full-length cDNA.

A full-length cDNA for the coding region of caGM-CSF was produced by PCR amplification of Exon I and the longest incomplete cDNA clone. The PCR product of this reaction was subcloned into pCMV, a mammalian expression vector with a CMV promoter. Four of these subclones were sequenced. Nucleotide misincorporation from the amplification reaction was noted in 3 of the 4 subclones. Each of these three subclones had 1, 2 and 5 base pair misincorporations, some of which were common to at least 2 subclones. The fourth clone had no misincorporations and was used to express the peptide for in vitro studies.

The nucleotide sequence for caGM-CSF is shown in FIGS. 2A and 4. There is an open reading frame beginning with the start codon "ATG" and ending at the stop codon "TGA", which is 432 bp in length and has an 80% sequence homology with the polynucleotide sequence corresponding to hGM-CSF. There is a 17 bp sequence which includes the start codon that is common to all four species from which GM-CSF has been isolated. The 3' region includes AT-rich sequences containing an ATTTA sequence motif. This feature is noted on other lymphokines, cytokines and proto oncogenes.

A comparison of all known amino acid sequences of GM-CSF is summarized in FIG. 5. The degree of homology between GM-CSF of dog and that of human, cow and mouse is 70%, 71%, and 53%, respectively. The comparison indicates that a 17 amino acid region typical of signal sequences precedes Ala-18 at the amino terminus of the mature polypeptide. The positions of the cysteine residues which are sites of disulfide bonds stabilizing secondary structure are conserved. There is one possible N-glycosylation site on caGM-CSF, compared to two on each of the other species. The N-glycosylation sites on murine GM-CSF are positioned differently, as compared to the other three types. Of the two regions associated with function in hGM-CSF [47,48], the stretch from amino acids 95–111 appears to be the most highly conserved portion to caGM-CSF.

Analysis of Canine Genomic DNA for GM-CSF

Figure 6:
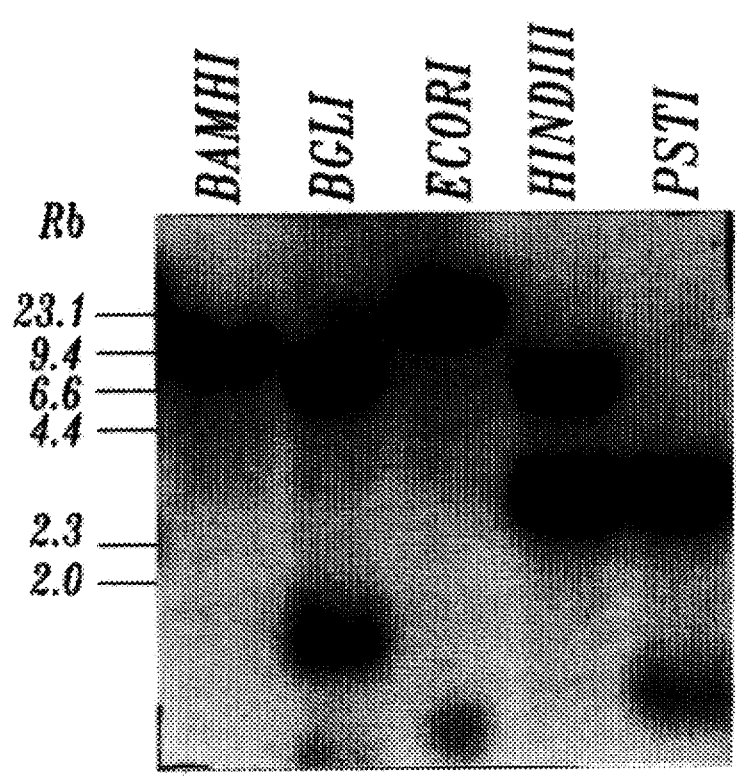
In FIG. 6, the blot was probed with $^{32}$P-labeled caGM-CSF cDNA. Restriction digests of DNA (10 μg) were with Bam HI, Bgl 1, Eco RI, Hind III, and PstI. Single bands were seen in BAM HI+Eco RI lanes suggesting that caGM-CSF is a single copy gene.

Canine genomic DNA was restriction digested and a Southern blot probed with $^{32}$P-labeled caGM-CSF (FIG. 6).

Single hybridizing bands were noted in lanes with DNA digested with Bam HI+Eco RI. This suggests that the gene for canine GM-CSF is single copy as has been shown for other species. In other lanes there were two hybridizing bands suggesting single internal restriction sites in the gene for Bgl I, Hind III, and Pst I.

Protein Expression and In Vitro Activity of CaGM-CSF

Figure 7:
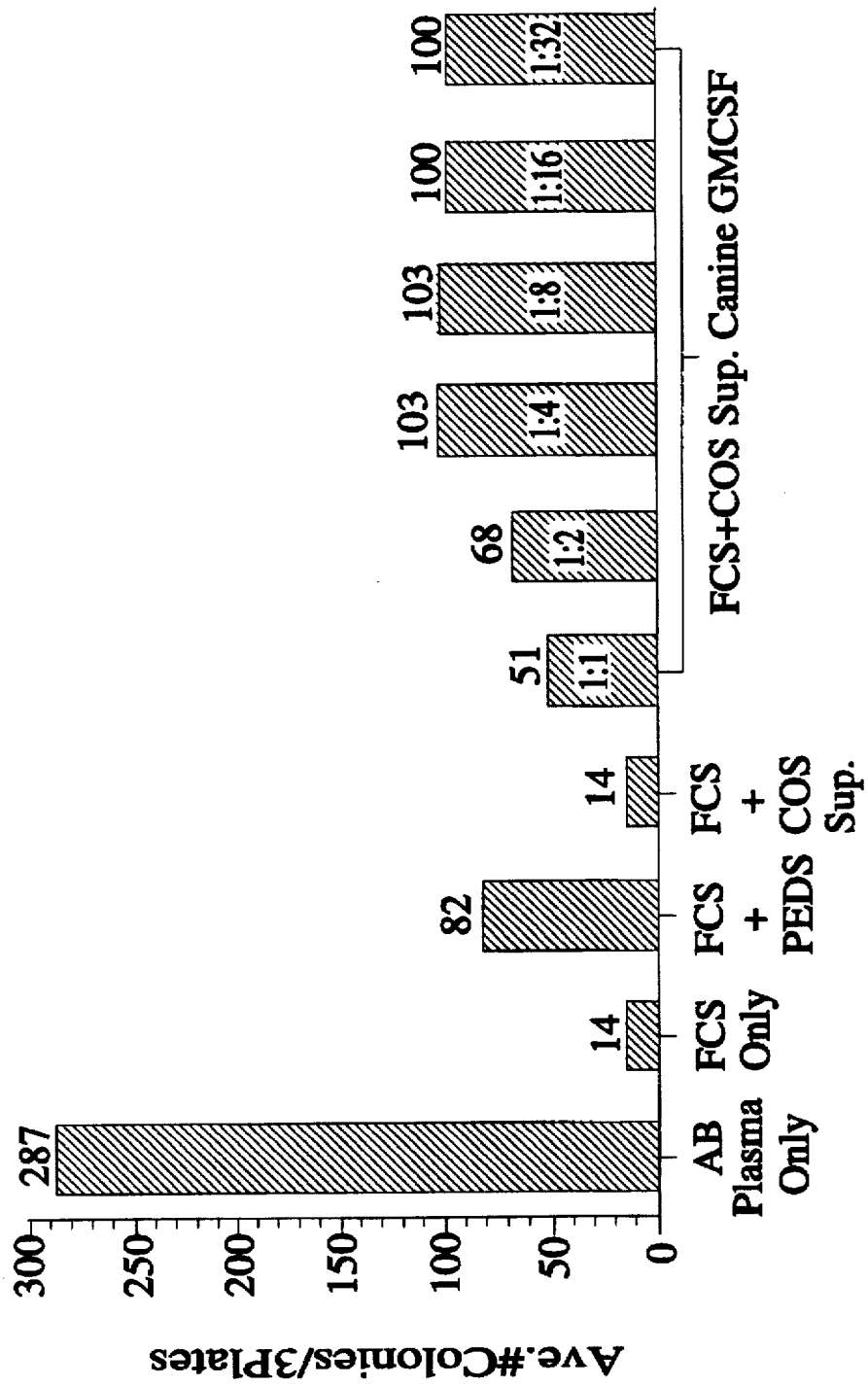
In FIG. 7, marrow mononuclear cells were collected from a Ficoll-Hypaque gradient, and depleted of monocytes and T-lymphocytes, and cultured at $7.5 \times 10^4$ cells/plate for 10 days. Different dilutions of supernatant enriched with caGM-CSF were added to the CFU-GM assays. Negative controls were assays with heat-inactivated Fetal Calf Serum only as well as assays that had supernatant from normal COS cells (not transfected). Positive controls were assays done with both 10% post endotoxin dog serum and also with human AB plasma.
Figure 8A:
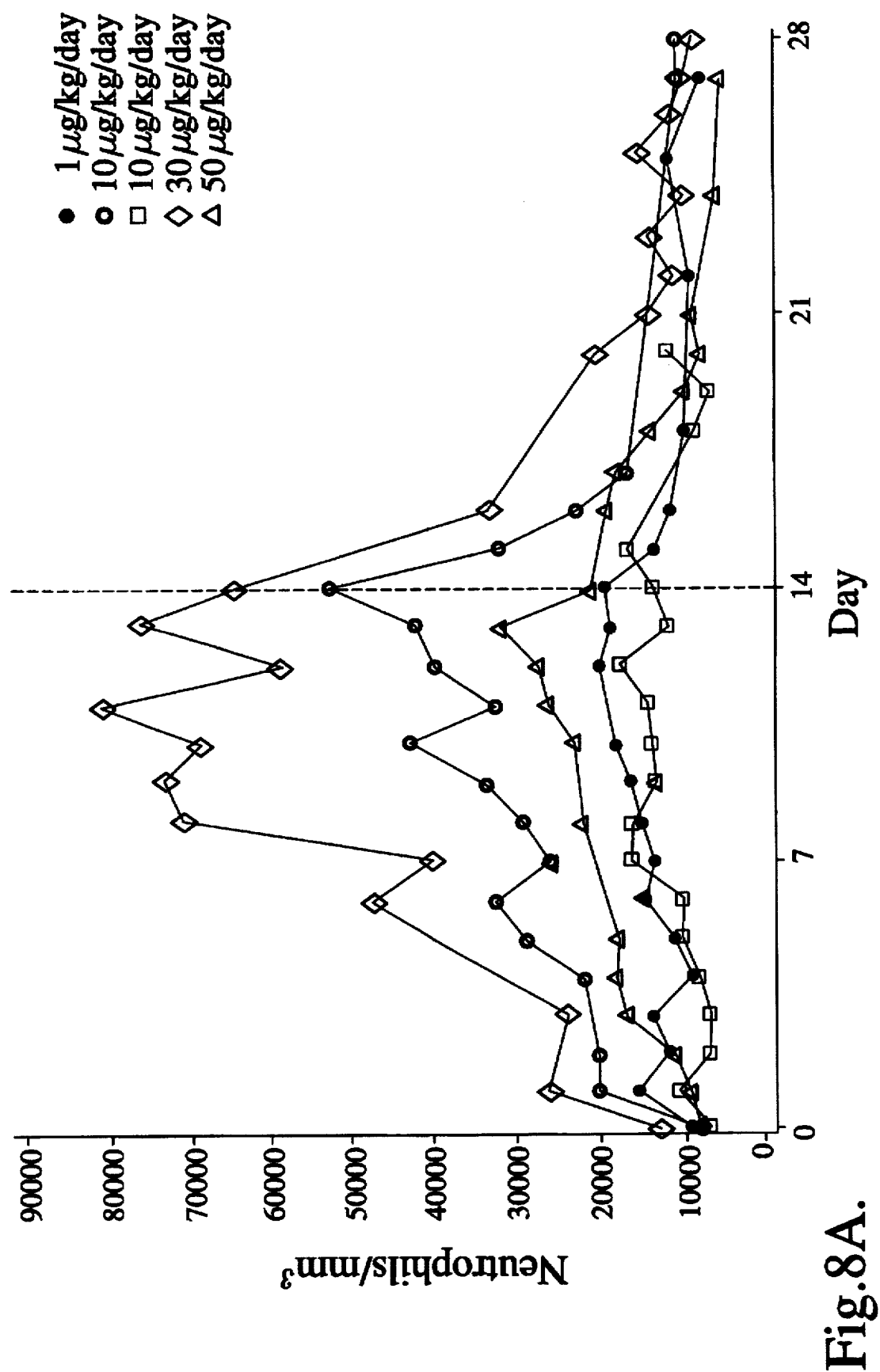
Figure 8B:
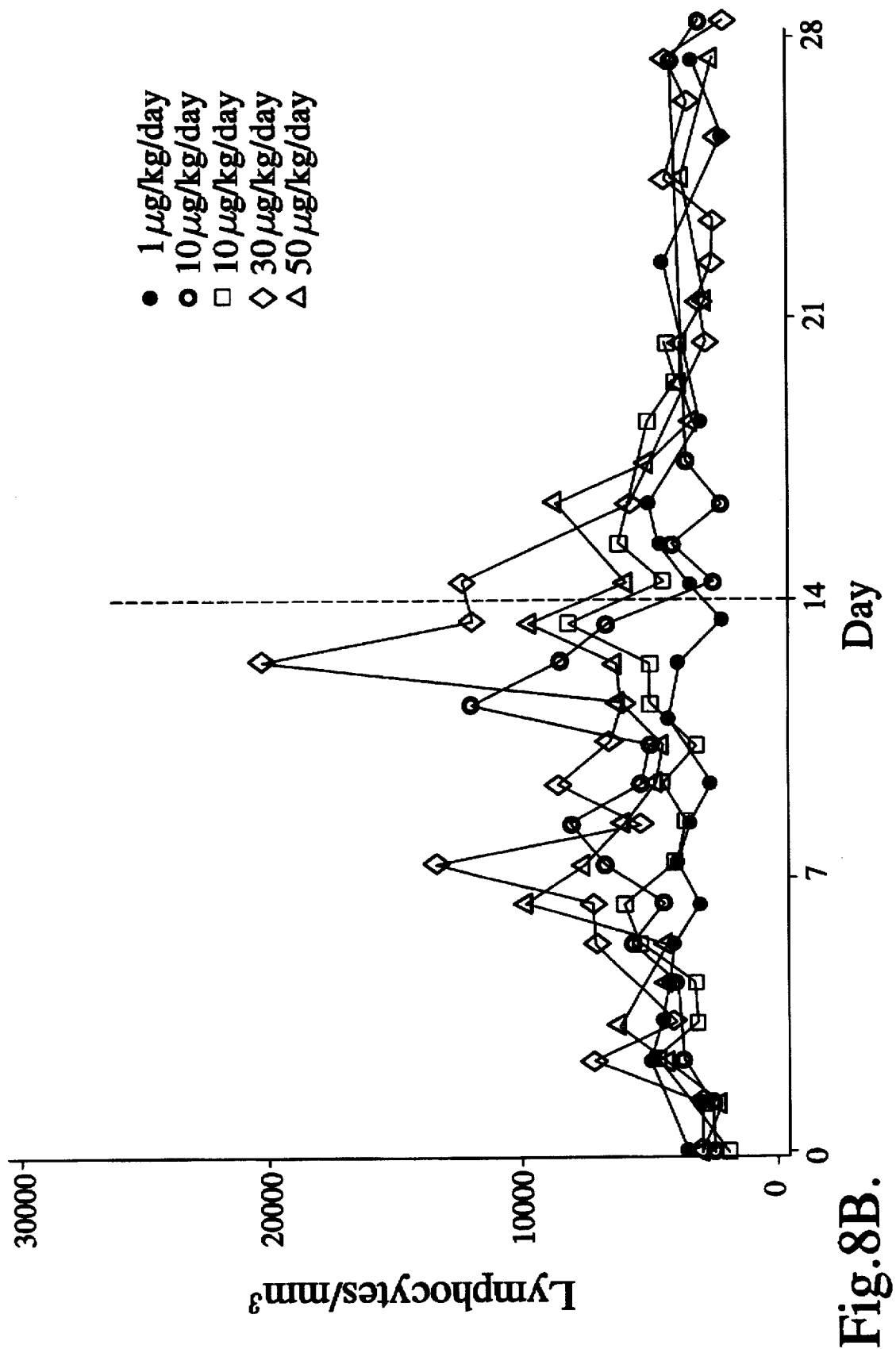
Figure 8C:
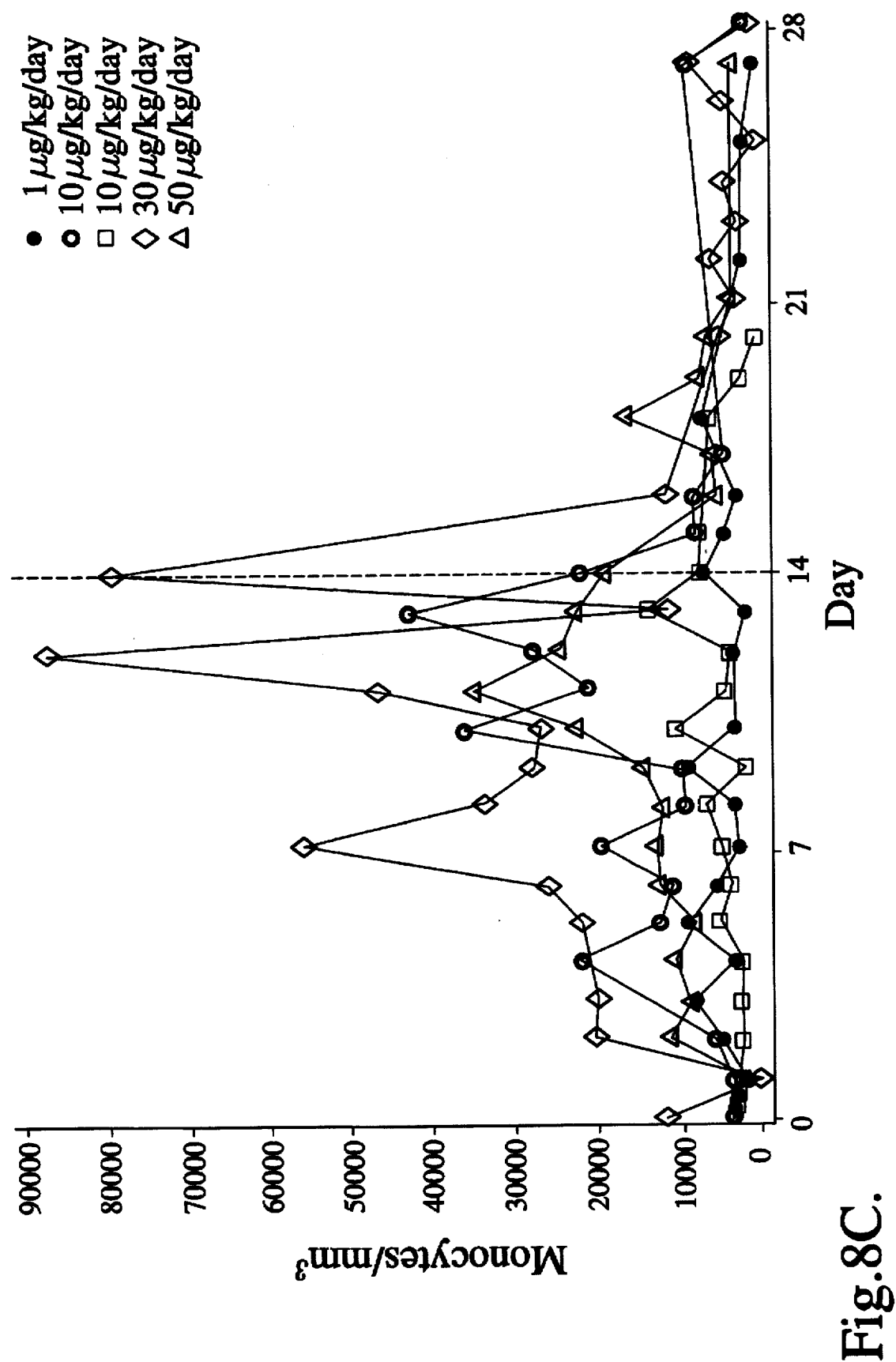
Figure 8D:
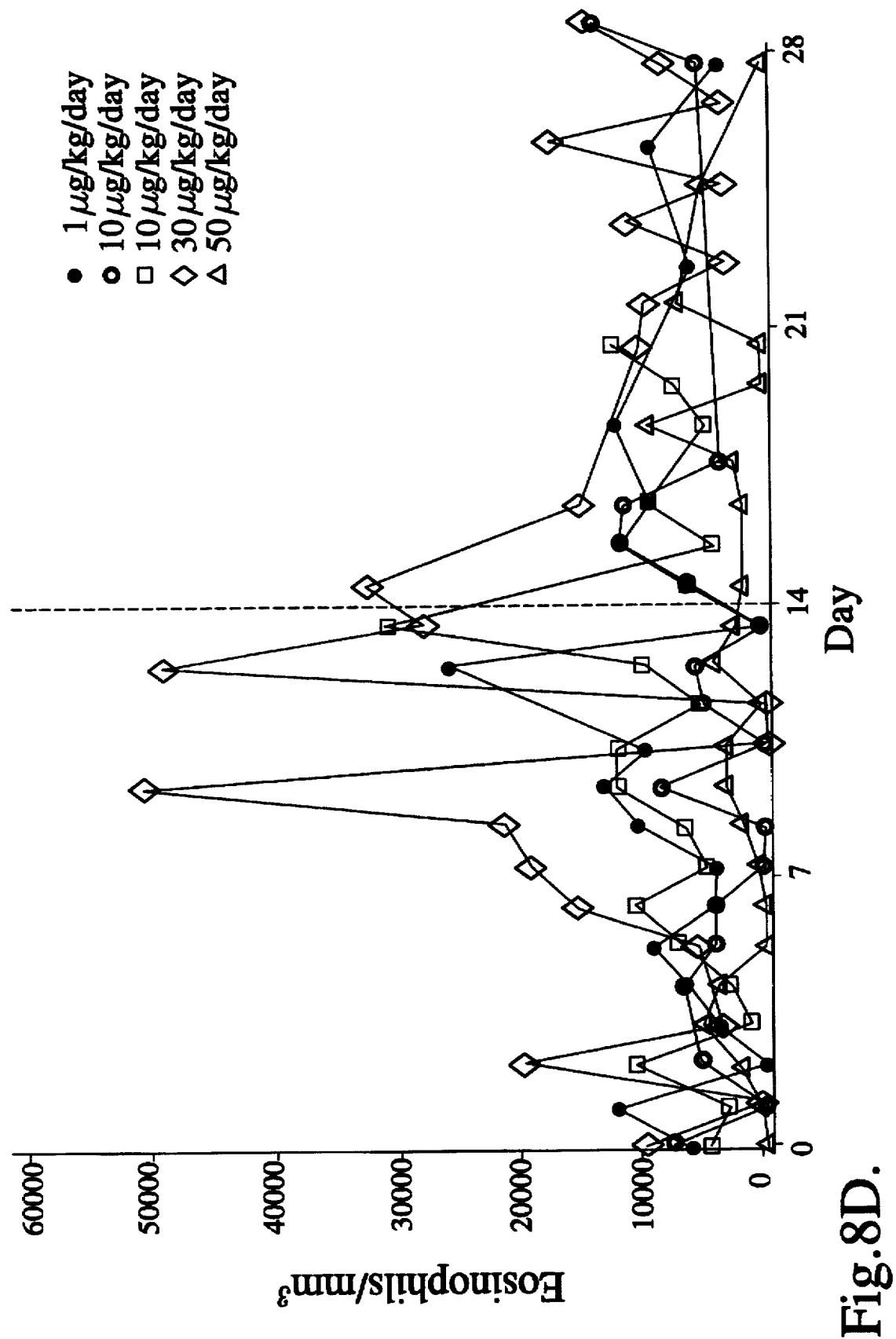

Transfection of COS cells for transient expression was done with the mammalian cell expression vector, pCMV/CAGM. Supernatant was collected at 72 and 120 hours after transfection for analysis of activity. Biologic activity was assessed by adding supernatant from transfected COS cells enriched for caGM-CSF at different dilutions to canine CFU-GM assays (FIG. 7). Culture plates without any addition of growth factor or with supernatant from COS cells that had not been transfected served as two negative controls. Plates with 10% post-endotoxin dog serum or with human AB plasma were the positive controls. The number of CFU-GM colonies formed in the caGM-CSF containing plates was 4- to 7-fold greater than the baseline established with the 2 negative controls and equivalent to the numbers of colonies obtained with addition of post-endotoxin dog serum.

In Vivo Activity of caGM-CSF

Four normal dogs were treated with caGM-CSF to assess the in vivo effect on hematopoiesis. Three dogs had a single dose schedule of 10 µg/kg/day, 30 µg/kg/day and 50 µg/kg/day for 14 days, administered subcutaneously twice daily. There was an increase in the peripheral blood neutrophil count, as well as the lymphocyte and monocyte count compared to pre-treatment baseline (FIG. 8). There was a suggestion of a rise in the absolute eosinophil count in the peripheral blood but this was more variable, being unremarkable in the dog receiving the 50 µg/kg/day dose. Day 14 marrow after treatment appeared more hypercellular at the higher does schedules, and there was evidence of increased mitotic activity. The fourth dog had two treatments in series of 1 µg/kg/day caGM-CSF administered for 14 days, followed by 14 days of rest and then 10 µg/kg/day caGM-CSF for another 14 days. At 1 µg/kg/day, the dog had a slight elevation in neutrophil count. When the 10 µg/kg/day dose was administered, the peripheral blood neutrophil count increased 6- to 7-fold when compared to the pre-treatment baseline. A residual effect of the first dose of caGM-CSF 14 days previously could explain the marked increase in peripheral blood counts compared to other animals that received similar or higher doses.

The platelet count decreased in all the animals within twenty-four hours of the start of treatment (FIG. 9). Platelets continued to decrease for 4–8 days of treatment before stabilizing at levels which were dose dependent. Platelet counts returned to normal within several days of stopping the caGM-CSF, starting to increase within 24–48 hours after the last dose. Peripheral blood smears demonstrated large platelets with no morphologic abnormalities similar to the clinical syndrome of idiopathic thrombocytopenia purpura. Examination of the marrows showed that megakaryocytes were normal to increased in frequency. Platelet survival studies with $^{51}$Cr-labeled autologous platelets were done in two dogs receiving the dose of 10 µg/kg/day and 50 µg/kg/day of caGM-CSF. Studies were done to establish the normal survival curves of platelets in each animal as well as in the first and second week of treatment. These studies showed a decreased survival of platelets from about 5 to 6 days normally to 1.5 to 2.0 days.

Discussion

The cDNA for canine GM-CSF has been cloned and the polypeptide expressed for in vitro and in vivo studies. The nucleotide sequence homology of the open reading frames between caGM-CSF and hGM-CSF is 80% There is a 5' stretch 17bp in length including the start codon which is the same in all four of the GM-CSF cDNAs from different species currently reported [1,2,37]. This may facilitate the cloning of GM-CSF cDNAs from other species. In the 3' untranslated region, there is an AT-rich region with an ATTTA motif which has been described as destabilizing mRNA transcripts that may be important for regulation of GM-CSF. This motif is highly conserved in GM-CSF cDNA from different species.

The gene for canine GM-CSF was shown to be a single copy in a Southern blot of restriction digested canine genomic DNA. The high degree of nucleotide and amino acid sequence homology between canine and human GM-CSF as well as the observation that this is a unique sequence in canine genomic DNA suggest that this molecule is in fact the canine homologue to human GM-CSF.

The in vitro biologic activity of the protein was confirmed by CFU-GM assays of canine marrow. The activity of caGM-CSF expressed from COS cells was similar to that of 10% post endotoxin dog serum in canine CFU-GM assays. Canine GM-CSF has also been demonstrated to stimulate human GM-CSF dependent cell lines such as Tall 101, but other human GM-CSF dependent cell lines may not be as responsive (Dale, D.). Human GM-CSF also stimulates in vivo canine hematopoiesis [38]. The cross-reactivity may be explained by the high degree of homology, especially in the region 95–111 amino acids. This is now another analogue for hGM-CSF which may be helpful in further defining regions of this molecule important for activity with human hematopoietic cells. The restricted GM-CSF activity between species which had been previously described seems less evident between canine and human forms.

When caGM-CSF was administered to normal dogs, there were increases in peripheral neutrophil, monocyte, and lymphocyte counts with increased marrow cellularity. The change in eosinophil counts was more variable. Thrombocytopenia developed in all dogs and appeared to be dose-dependent. Normal to increased numbers of megakaryocytes in the marrow and decreased platelet survival times implicated increased consumption as the mechanism. Whether production of platelets is affected is harder to determine, but the large platelets in the peripheral blood and the rapid rise in platelet counts after stopping caGM-CSF suggest some increased production. Increased production might be expected from direct or indirect stimulation of megakaryocytes by caGM-CSF or as a physiologic response to the thrombocytopenia. Thrombocytopenia also developed in dogs receiving hGM-CSF, and increased consumption was demonstrated as well by determining platelet survival times [38].

The in vivo effect of GM-CSF on megakaryocytes and platelets is not well delineated. Platelet counts varied in different animal studies with no changes observed in mice treated with mGM-CSF [50] and platelets noted as unchanged, decreased or increased in primates treated with hGM-CSF [25,51,53] (Farese, A.). Thrombocytopenia has been reported as a complication in several clinical studies of patients with cancer or acquired immunodeficiency syndrome receiving hGM-CSF [52–54]. The possibility of exacerbation of an otherwise stable or subclinical autoimmune thrombocytopenia was considered for some patients. It has also been reported in patients with aplastic anemia that platelet counts 1 hour after platelet transfusion were lower, while on treatment with hGM-CSF, were comparable to pre-treatment increments [55]. Other studies have shown no significant change, or, in some patients with myelodysplasia, an increase in platelet counts [28,29]. There are reports of more rapid recovery of platelet count after autologous marrow transplantation [26,32].

Following peripheral blood counts to assess the in vivo effect of GM-CSF on megakaryocytes and platelets is problematic since the platelet count is the result of a dynamic equilibrium between production and consumption of platelets. If GM-CSF increased both production and consumption of platelets, it could yield no change in peripheral counts but some event such as a disease process or treatment could change the equilibrium and increase or decrease counts depending on how production or consumption is affected. Studies on production and utilization of platelets will be necessary to assess the in vivo effects of GM-CSF. Assessment of the thrombocytopenia that develops in normal dogs with no predisposing factors may allow a better biological description of an important side effect observed in some patients receiving hGM-CSF. This model may also be useful because this mechanism, where thrombocytopenia may be induced directly or indirectly by abnormal amounts of a physiologic cytokine like GM-CSF, may also be operative in some disease processes.

Canine GM-CSF has been cloned and expressed and will be useful in analyzing questions about the in vivo biological activities of GM-CSF in this animal model. It may also have therapeutic applications in veterinary practice to lessen hematologic toxicity of chemotherapy or as an adjuvant in treatment of infections. Thrombocytopenia is a reproducible dose-dependent phenomenon in normal dogs receiving the species-specific GM-CSF. The decreased survival of platelets as a result of the in vivo administration of GM-CSF may also occur in other species, but other variables such as disease processes or chemotherapy may need to be operative to observe significant changes in platelet counts.

Bibliography

1. Gough N M, Gough J, Metcalf D, Kelso A, Grail D, Nicola N A, Burgess A W, Dunn A R: Molecular cloning of cDNA encoding a murine hematopoietic growth regulator, granulocyte-macrophage colony stimulating factor. Nature 309:763, 1984.
2. Wong G G, Witek J S, Temple P A, Wilkens K M, Leary A C, Luxenberg D P, Jones S S, Brown E L, Kay R M, Orr E C, Shoemaker C, Golde D W, Kaufman R J, Hewick R M, Wang E A, Clark S C: Human GM-CSF: Molecular cloning of the complementary DNA and purification of the natural and recombinant proteins. Science 228:810, 1985.
3. Clark S C, Kamen R: The human hematopoietic colony-stimulating factors. Science 236:1229, 1987.
4. Kelso A, Metcalf D: Clonal heterogeneity in colony stimulating factor production by murine T lymphocytes. J Cell Physiol 123:101, 1985.
5. Thorens B, Mermod J-J, Vassalli P: Phagocytosis and inflammatory stimuli induce GM-CSF mRNA in macrophages through post-transcriptional regulation. Cell 48:671, 1987.
6. Malone D G, Pierce J H, Falko J P, Metcalfe D D: Production of granulocyte-macrophage colony-stimulating factor by primary cultures of unstimulated rat microvascular endothelial cells. Blood 71(3):684, 1988.
7. Kaushansky K, Lin N, Adamson J W: Interleukin 1 stimulates fibroblasts to synthesize granulocyte-macrophage and granulocyte colony-stimulating factors. J Clin Invest 81:92, 1988.
8. Chodakewitz J A, Kupper T S, Coleman D L: Keratinocyte-derived granulocyte/macrophage colony-stimulating factor induces DNA synthesis by peritoneal macrophages. J Immunol 140:832, 1988.
9. Horowitz M C, Coleman D L, Flood P M, Kupper T S, Jilka R L: Parathyroid hormone and lipopolysaccharide induce murine osteoblast-like cells to secrete a cytokine indistinguishable from granulocyte-macrophage colony stimulating factor. J Clin Invest 83:149, 1989.
10. Sieff C A: Hematopoietic growth factors. J Clin Invest 79:1549, 1987.
11. Sieff C A, Emerson S G, Donahue R E, Nathan D G, Wang E A, Wong G G, Clark S C: Human recombinant granulocyte-macrophage colony-stimulating factor: A multilineage hematopoietin. Science 230:1171, 1985.
12. Metcalf D, Burgess A W, Johnson G R, Nicola N A, Nice E C, DeLamarter J, Thathcher D R, Mermod J J: In vitro actions on hemopoietic cells of recombinant murine GM-CSF purified after production in *Escherichia coli*: comparison with purified native GM-CSF. J Cell Physiol 128:421, 1986.
13. Metcalf D, Begley C G, Johnson G R, Nicola N A, Vadas M A, Lopez A F, Williamson D J, Wong G G, Clark S C, Wang E A: Biologic properties in vitro of a recombinant human granulocyte-macrophage colony-stimulating factor. Blood 67:37, 1986.
14. Tomonaga M, Golde D W, Gasson J C: Biosynthetic (recombinant) human granulocyte-macrophage colony-stimulating factor: Effect on normal bone marrow and leukemia cell lines. Blood 67:31, 1986.
15. Emerson S G, Yang Y C, Clark S C, Long M W: Human recombinant granulocyte-macrophage colony stimulating factor and interleukin 3 have overlapping but distinct hematopoietic activities. J Clin Invest 82:1282, 1988.
16. Donahue R E, Emerson S G, Wang E A, Wong G G, Clark S C, Nathan D G: Demonstration of burst-promoting activity of recombinant human GM-CSF on circulating erythroid progenitors using an assay involving the delayed addition of erythropoietin. Blood 66(6):1479, 1985.
17. Ferrero D, Tarella C, Badoni R, Caracciolo D, Bellone G, Pileri A, Gallo E: Granulocyte-macrophage colony-stimulating factor requires interaction with accessory cells or granulocyte-colony stimulating factor for full stimulation of human myeloid progenitors. Blood 73(2):402, 1989.
18. Wang J M, Colella S, Allavena P, Montovani A: Chemotactic activity of human recombinant granulocyte-macrophage colony-stimulating factor. Immunology 60:439, 1987.
19. Nathan C: Respiratory burst in adherent human neutrophils: Triggering by colony-stimulating factors CSF-GM and CSF-G. Blood 73(1):301, 1989.
20. Weisbart R H, Kwan L, Golde D W, Gasson J C: Human GM-CSF primes neutrophils for enhanced oxidative metabolism in response to the major physiological chemoattractants. Blood 69(1):18, 1987.
21. Fleischmann J, Golde D W, Weisbart R H, Gasson J C: Granulocyte-macrophage colony-stimulating factor enhances phagocytosis of bacteria by human neutrophils. Blood 68(3):708, 1986.
22. Villalta F, Kierszenbaum F: Effects of human colony-stimulating factor on the uptake and destruction of a pathogenic parasite (*Trypanosoma cruzi*) by human neutrophils. J Immunol 137:1703, 1986.
23. Morrissey P J, Bressler L, Park L S, Alpert A, Gillis S: Granulocyte-macrophage colony-stimulating factor augments the primary antibody response by enhancing the function of antigen-presenting cells. J Immunol 139:1113, 1987.

24. Robinson B E, McGrath H E, Quesenberry P J: Recombinant murine granulocyte-macrophage colony-stimulating factor has megakaryocyte colony stimulating activity and augments megakaryocyte colony stimulation by Interleukin 3. J Clin Invest 79:1648, 1987.

25. Donahue R E, Wang E A, Stone D K, Kamen R, Wong G G, Sehgal P K, Nathan D G, Clark S C: Stimulation of hematopoiesis in primates by continuous infusion of recombinant human GM-CSF. Nature 321(6073):872, 1986.

26. Neinhuis A W, Donahue R E, Karlsson S, Clark S E, Agricola B, Antinoff N, Pierce J E, Turner P, Anderson W F, Nathan D G: Recombinant granulocyte-macrophage colony-stimulating factor (GM-CSF) shortens the period of neutropenia after autologous bone marrow transplantation in a primate model. J Clin Invest 80:573, 1987.

27. Monroy R L, Skelly R R, MacVittie T J, Davis T A, Sauber J J, Clark S C, Donahue R E: The effect of recombinant GM-CSF on the recovery of monkeys transplanted with autologous bone marrow. Blood 70(5):1696, 1987.

28. Groopman J E, Mitsuyasu R T, DeLeo M J, Oette D H, Golde D W: Effect of recombinant human granulocyte-macrophage colony-stimulating factor on myelopoiesis in the acquired immunodeficiency syndrome. N Engl J Med 317:593, 1987.

29. Vadhan-Raj S, Keating M, LeMaistre A, Hittleman W N, McCredie K, Trujillo J M, Broxmeyer H E, Henney C, Gutterman J U: Effects of recombinant human granulocyte-macrophage colony-stimulating factor in patients with myelodysplastic syndromes. N Engl J Med 317:1545, 1987.

30. Antman K S, Griffin J D, Elias A, Socinski M A, Ryan L, Cannistra S A, Oette D, Whitley M, Frei E, Schnipper L E: Effect of recombinant human granulocyte-macrophage colony-stimulating factor on chemotherapy-induced myelosuppression. N Engl J Med 319:593, 1988.

31. Brandt S J, Peters W P, Atwater S K, Kurtzberg J, Borowitz M J, Jones R B, Shpall E J, Bast R C, Gilbert C J, Oette D H: Effect of recombinant human granulocyte-macrophage colony-stimulating factor on hematopoietic reconstitution after high-dose chemotherapy and autologous bone marrow transplantation. N Engl J Med 318:869, 1988.

32. Nemunaitis J, Singer J W, Buckner C D, Hill R, Storb R, Thomas E D, Appelbaum F R: Use of recombinant human granulocyte-macrophage colony-stimulating factor in autologous marrow transplantation for lymphoid malignancies. Blood 72(2):834, 1988.

33. Ladiges W C, Storb R, Thomas E D: Canine models of bone marrow transplantation. Lab Anim Sci 40:11, 1990.

34. Appelbaum F R, Brown P, Sandmaier B, Badger C, Schuening F, Graham T, Storb R: Antibody-radionuclide conjugates as part of a myeloablative preparative regimen for marrow transplantation. Blood 73(8):2202, 1989.

35. Deeg H J, Graham T C, Gerhard-Miller L, Appelbaum F R, Schuening F, Storb R: Prevention of transfusion-induced graft-versus-host disease in dogs by ultraviolet irradiation. Blood 74(7):2592, 1989.

36. Schuening F G, Storb R, Goehle S, Graham T C, Appelbaum F R, Hackman R, Souza L M: Effect of recombinant human granulocyte colony-stimulating factor on hematopoiesis of normal dogs and on hematopoietic recovery after otherwise lethal total body irradiation. Blood 74(4):1308, 1989.

37. Maliszewski C R, Schoenborn M A, Cerretti D P, Wignall J M, Picha K S, Cosman D, Tushinski R J, Gillis S, Baker P E: Bovine GM-CSF: Molecular cloning and biological activity of the recombinant protein. Mol Immunol 25:843, 1988.

38. Schuening F G, Storb R, Goehle S, Nash R, Graham T C, Appelbaum F R, Hackman R, Sandmaier B M, Urdal D L: Stimulation of canine hematopoiesis by recombinant human granulocyte-macrophage colony-stimulating factor. Exp Hematol 17:889, 1989.

39. Maniatis T, Fritsch E F, Sambrook J: Molecular Cloning: A Laboratory Manual. New York, Cold Spring Harbor, 1982.

40. Short J M, Fernandez J M, Sorge J A, Huse W D: ZAP: a bacteriophage expression vector with in vivo excision properties. Nucleic Acids Res 16:7583, 1988.

41. Feinberg A P, Vogelstein B: A technique for radiolabeling DNA restriction endonuclease fragments to high specific activity. Anal Biochem 132:6, 1983.

42. Saiki R K, Gelfand D H, Stoffel S, Scharf S J, Higuchi R, Horn G T, Mullis K B, Erlich H A: Primer-directed enzymatic amplification of DNA with a thermostable DNA polymerase. Science 239:487, 1988.

43. Sanger F, Nicklen S, Coulson A R: DNA sequencing with chain-terminating inhibitors. Proc Natl Acad Sci USA 74(12):5463, 1977.

44. Graham F L, Van Der Eb A J: A new technique for the assay of infectivity of human adenovirus 5 DNA. Virology 52:456, 1973.

45. Kaushansky K, O'Hara P J, Hart C E, Forstrom J W, Hagen F S: Role of carbohydrate in the function of human granulocyte-macrophage colony-stimulating factor. Biochemistry 26:4861, 1987.

46. Slichter S J, Deeg H J, Kennedy M S: Prevention of platelet alloimmunization in dogs with systemic cyclosporin and by UV-irradiation or cyclosporin-loading of donor platelets. Blood 69(2):414, 1987.

47. Kaushansky K, Shoemaker S G, Alfaro S, Brown C: Hematopoietic activity of granulocyte/macrophage colony-stimulating factor is dependent upon two distinct regions of the molecule: Functional analysis based upon the activities of interspecies hybrid growth factors. Proc Natl Acad Sci USA 86:1213, 1989.

48. Clark-Lewis I, Lopez A F, To L B, Vadas M A, Schrader J W, Hood L E, Kent S B H: Structure-function studies of human granulocyte-macrophage colony-stimulating factor. J Immunol 141:881, 1988.

49. Cebon J, Nicola N, Ward M, Gardner I, Dempsey P, Layton J, Dührsen U, Burgess A W, Nice E, Morstyn G: Granulocyte-macrophage colony stimulating factor from human lymphocytes. J Biol Chem 265(8):4483, 1990.

50. Metcalf D, Begley C G, Williamson D J, Nice E D, De Lamarter J, Mermod J, Thatcher D, Schmidt A: Hemopoietic responses in mice injected with purified recombinant murine GM-CSF. Exp Hematol 15:1, 1987.

51. Monroy R L, Davis T A, MaeVittie T J: Short analytical review: granulocyte-macrophage colony-stimulating factor: more than a hemopoietin. Clin Immunol Immunopathol 54:333, 1990.

52. Levine J D, Allan J D, Tessitore J H, Falcone N, Israel R, Groopman J E: Granulocyte-macrophage colony stimulating factor ameliorates the neutropenia induced by azidothymidine in AIDS/ARC patients. Proceedings of ASCO 8:1, 1989 (abstr).

53. Scadden D, Bering H, Levine J, Allen D, Bresnahan J, Epstein C, Evans L, Groopman J: Combined AZT/interferon-alpha/GM-CSF for AIDS-associated Kaposi's Sarcoma (KS). Blood 74(7):127a, 1989 (abstr).

54. Lieschke G J, Maher D, Cebon J, O'Connor M, Green M, Sheridan W, Boyd A, Rallings M, Bonnem E, Metcalf D, Burgess A W, McGrath K, Fox, R M, Morstyn G: Effects of bacterially synthesized recombinant human granulocyte-macrophage colony-stimulating factor in patients with advanced malignancy. Ann Intern Med 110:357, 1989.

55. Higgins M J, Leitman S F, Read E J, Young N S: Diminished response to platelet transfusions in aplastic anemia patients receiving GM-CSF. Transfusion 29:36S, 1989 (abstr).

The invention now being fully described, it will be apparent to one of ordinary skill in the art that many changes and modifications can be made thereto, without departing from the spirit or scope of the invention as set forth herein.

The embodiments of the invention in which an exclusive property or privilege is claimed are defined as follows:

1. An isolated DNA molecule, which encodes Amino Acid Sequence I (SEQ ID NO:1).
2. An isolated DNA molecule, which encodes Amino Acid Sequence II (SEQ ID NO:2).
3. An isolated DNA molecule, which encodes Amino Acid Sequence III (SEQ ID NO:3).
4. An isolated DNA molecule, which comprises the nucleotide sequence I (SEQ ID NO:6).
5. An isolated DNA molecule, which comprises the nucleotide sequence II (SEQ ID NO:7).
6. A recombinant expression vector comprising a DNA molecule according to any one of claims 1–5.
7. A cell transformed by an expression vector according to claim 6.
8. A cell according to claim 7, wherein said cell is that of a prokaryote.
9. A cell according to claim 7, wherein said cell is that of a eukaryote.
10. A cell according to claim 9, wherein said eukaryote is yeast.
11. A cell according to claim 9, wherein said eukaryote is a mammal.
12. A cell according to claim 11, which is a COS cell.
13. A method of producing a proteinaceous molecule having an activity of canine granulocyte macrophage colony stimulating factor, which comprises culturing a cell according to claim 7 for a time sufficient to produce said proteinaceous molecule.

* * * * *

UNITED STATES PATENT AND TRADEMARK OFFICE
CERTIFICATE OF CORRECTION

PATENT NO. : 5,702,919
DATED : December 30, 1997
INVENTOR(S) : R.A. Nash et al.

It is certified that error appears in the above-indentified patent and that said Letters Patent is hereby corrected as shown below:

COLUMN     LINE

[56] Refs. Cited (U.S. Pat. Docs.)    Please insert the following references:
Pg. 1, col. 2

--4,135,975   01/23/1979   Lichtman et al. . . . 195/1.8
4,591,557   05/27/1986   Keyes et al. . . . . 435/68
4,621,050   11/04/1986   Sugimoto . . . . . . 435/68
5,106,733   04/21/1992   Baker et al. . . . . 435/69.5--

[56] Refs. Cited (Other Publs.)    Please insert the following references:
Pg. 1, col. 2

--Nash et al., "Canine Granulocyte Macrophage-Colony Stimulating Factor (GM-CSF): Cloning The cDNA," *Experimental Hematology* 18:622 (1990).

Wong et al., "Human GM-CSF: Molecular Cloning of the Complementary DNA and Purification of the Natural and Recombinant Proteins," *Science* 228:810-815 (1985).

Hammond et al., "A Comparison of Treatment of Canine Cyclic Hematopoiesis With Recombinant Human Granulocyte-Macrophage Colony-Stimulating Factor (GM-CSF), G-CSF, Interleukin-3, and Canine G-CSF," *Blood* 76:523-532 (1990).

D. Metcalf et al., "Biologic Properties In Vitro of A Recombinant Human Granulocyte-Macrophage Colony-Stimulating Factor," *Blood* 67:37-45 (1986).

UNITED STATES PATENT AND TRADEMARK OFFICE
CERTIFICATE OF CORRECTION

PATENT NO. : 5,702,919
DATED : December 30, 1997
INVENTOR(S) : R.A. Nash et al.

Page 2 of 3

It is certified that error appears in the above-identified patent and that said Letters Patent is hereby corrected as shown below:

COLUMN     LINE

[56] Pg. 1, col. 2    Refs. Cited (Other Publs.)    C.R. Maliszewski et al., "Bovine GM-CSF: Molecular Cloning and Biological Activity of the Recombinant Protein," *Molecular Immunology* 25:843-850 (1988).

*(continued)*    F.G. Schuening et al., "Stimulation of Canine Hematopoiesis by Recombinant Human Granulocyte-Macrophage Colony-Stimulating Factor," *Experimental Hematology* 17:889-894 (1989).

N.M. Gough et al., "Molecular Cloning of cDNA Encoding a Murine Haematopietic Growth Regulator, Granulocyte-Macrophage Colony Stimulating Factor," *Nature* 309:763-767 (1984).

R. Lewin, "When does homology mean something else?", *Science*, Vol. 237, 25 September 1987.

G.R. Reeck et al., *Cell*, 1987, Vol. 50, pg. 667.

P. Mayer et al., *Experimental Hematology* 18(9), 1990, pgs. 1026-33 (Abstract only).

Montes et al., *CA*, Vol. 104, 1986, #223220p.--

[56] Pg. 1, col. 2    Refs. Cited (Publs.)    "Vowie" should read --Bowie--

UNITED STATES PATENT AND TRADEMARK OFFICE
CERTIFICATE OF CORRECTION

PATENT NO. : 5,702,919  
DATED : December 30, 1997  
INVENTOR(S) : R.A. Nash et al.

Page 3 of 3

It is certified that error appears in the above-indentified patent and that said Letters Patent is hereby corrected as shown below:

| COLUMN | LINE | |
|---|---|---|
| 3 | 4 | "homotogy" should read --homology-- |
| 3 | 17-18 | "has (SEQ ID NO:1)" should read --(SEQ ID NO:1) has-- |
| 3 | 30 | "HI+Eco RI" should read --H1 + Eco R1-- |
| 5 | 21 | "Set-17" should read --Ser-17-- |
| 6 | 67 | "Pseudomonas" should appear in character italics |
| 7 | 48 | "vital" should read --viral-- |
| 8 | 43 | "αdeoxy-cytidine" should read --α deoxy-cytidine-- |
| 16 (#51, line 1) | 53 | "MaeVittie" should read --MacVittie-- |

Signed and Sealed this

Fourth Day of May, 1999

Attest:

Q. TODD DICKINSON

*Attesting Officer*    *Acting Commissioner of Patents and Trademarks*